United States Patent
Mujwid et al.

(10) Patent No.: US 11,376,410 B2
(45) Date of Patent: Jul. 5, 2022

(54) BODILY IMPLANT WITH A TUBING CONNECTOR

(71) Applicant: Boston Scientific Scimed, Inc., Maple Grove, MN (US)

(72) Inventors: James Ryan Mujwid, Hudson, WI (US); Ryan Earl Fredrick, Eden Prairie, MN (US); John Anders Bostrom, Saint Paul, MN (US); Mark Edward DiLoreto, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 323 days.

(21) Appl. No.: 16/401,481

(22) Filed: May 2, 2019

(65) Prior Publication Data

US 2019/0336745 A1 Nov. 7, 2019

Related U.S. Application Data

(60) Provisional application No. 62/667,900, filed on May 7, 2018.

(51) Int. Cl.
*A61M 39/10* (2006.01)
*A61F 2/00* (2006.01)
*A61F 2/26* (2006.01)

(52) U.S. Cl.
CPC ......... *A61M 39/1011* (2013.01); *A61F 2/004* (2013.01); *A61F 2/26* (2013.01); *A61F 2250/0003* (2013.01); *A61F 2250/0013* (2013.01)

(58) Field of Classification Search
CPC ... A61M 39/10; A61M 39/1011; A61F 2/004; A61F 2/26
See application file for complete search history.

(56) References Cited

U.S. PATENT DOCUMENTS

| 4,214,586 A * | 7/1980 | Mericle ............... A61B 17/11 606/154 |
| 4,291,698 A * | 9/1981 | Fuchs ............... A61B 17/0487 606/232 |
| 4,723,948 A | 2/1988 | Clark et al. |
| 2005/0137614 A1 * | 6/2005 | Porter ............... A61M 1/3661 606/153 |
| 2013/0060268 A1 | 3/2013 | Herrig |

(Continued)

FOREIGN PATENT DOCUMENTS

FR 3007813 A1 1/2015

OTHER PUBLICATIONS

International Search Report and Written Opinion for Application No. PCT/US2019/030928, dated Oct. 15, 2019, 21 pages.

*Primary Examiner* — John P Lacyk
(74) *Attorney, Agent, or Firm* — Brake Hughes Bellermann LLP

(57) ABSTRACT

According to an aspect, a bodily implant includes a connector configured to connect a first tube member and a second tube member such that fluid can be transferred through the first tube member and the second tube member. The connector includes a first clip member having an inner surface, a second clip member having an inner surface, a hinge member coupled to the first clip member and the second clip member, a retaining member coupled to the inner surface of the second clip member, and an inner connector coupled to the retaining member.

19 Claims, 26 Drawing Sheets

(56) References Cited

U.S. PATENT DOCUMENTS

| | | | |
|---|---|---|---|
| 2014/0018829 A1* | 1/2014 | Patani | A61B 17/0487 |
| | | | 606/151 |
| 2015/0308598 A1 | 10/2015 | Lewis et al. | |
| 2016/0186906 A1* | 6/2016 | Blake | F16L 33/025 |
| | | | 285/319 |
| 2019/0247042 A1* | 8/2019 | Khairkhahan | A61B 17/0469 |

* cited by examiner

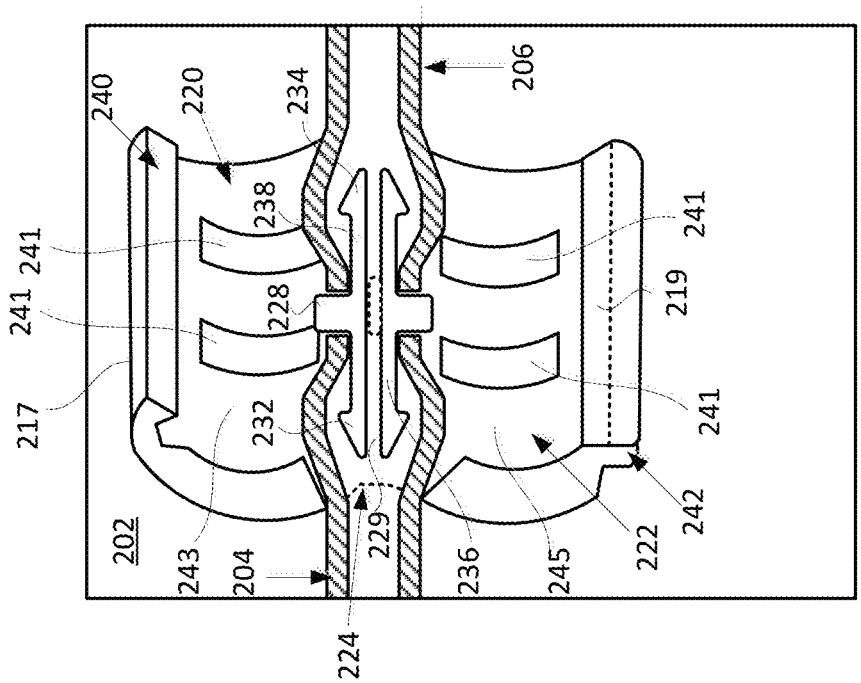
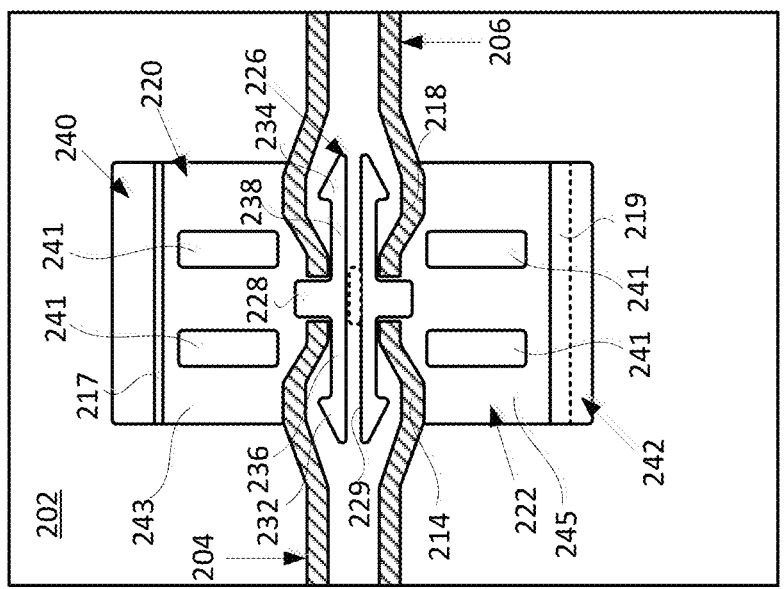
FIG. 2C
FIG. 2B

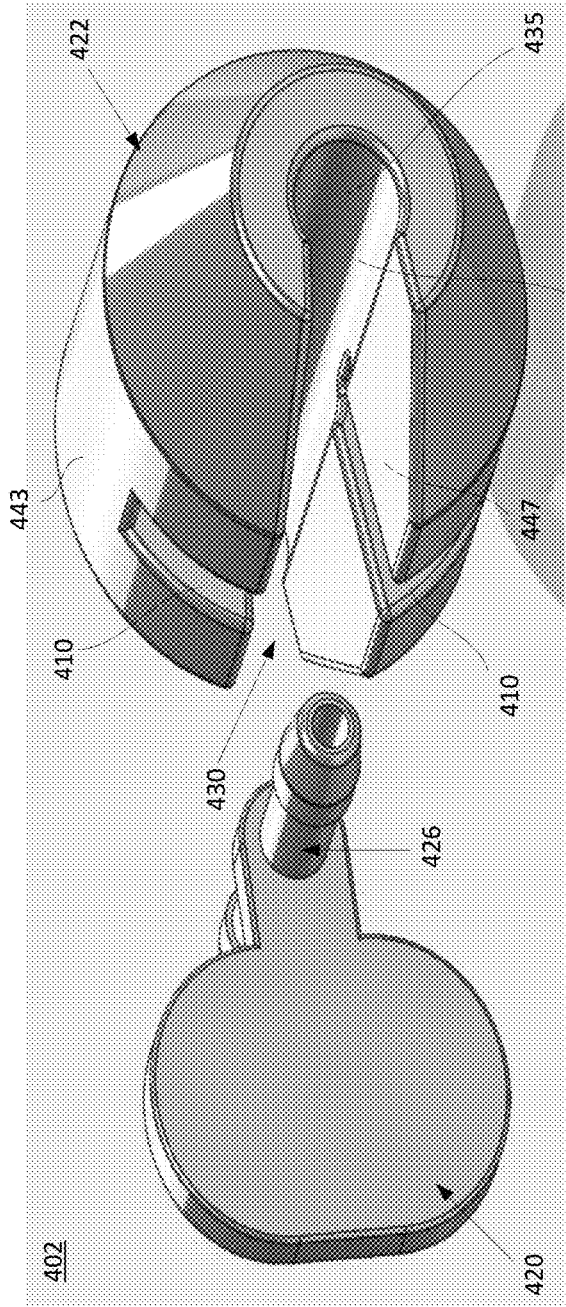
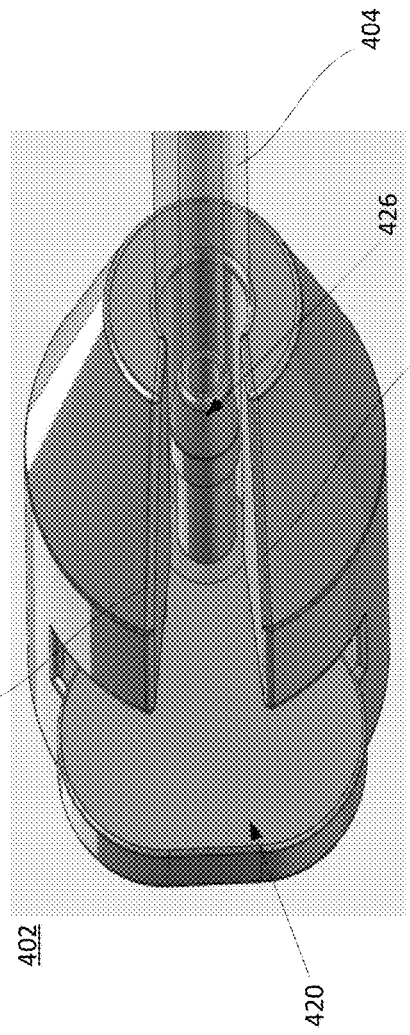
FIG. 4A
FIG. 4B

BODILY IMPLANT WITH A TUBING CONNECTOR

CROSS-REFERENCE TO RELATED APPLICATION

This application is a Nonprovisional of, and claims priority to, U.S. Patent Application No. 62/667,900, filed on May 7, 2018, entitled "BODILY IMPLANT WITH A TUBING CONNECTOR", which is incorporated by reference herein in its entirety.

TECHNICAL FIELD

This disclosure relates generally to bodily implants and more specifically to bodily implants having a connector for connecting tube members to transfer fluid.

BACKGROUND

A bodily implant may need to transfer fluid from one component (implanted in a part of the body) to another component (implanted in another part of the body). One tube member may need to be connected to another tube member in order to allow the fluid to be transferred between the components. In some examples, the tube members may be connected together with the assistance of a specialized assembly tool. However, the connection process may be cumbersome due to the higher amount of small pieces that must be assembled by the physician within the body of the patient using the specialized assembly tool.

SUMMARY

According to an aspect, a bodily implant includes a connector configured to connect a first tube member and a second tube member such that fluid can be transferred through the first tube member and the second tube member. The connector includes a first clip member having an inner surface, a second clip member having an inner surface, a hinge member coupled to the first clip member and the second clip member, a retaining member coupled to the inner surface of the second clip member, and an inner connector coupled to the retaining member.

According to some aspects, the bodily implant may include one or more of the following features (or any combination thereof). The inner connector is movably coupled to the retaining member. The retaining member includes an opening and a retaining clip that is coupled to the second clip member, where a portion of the inner connector is disposed within the opening. The connector is configured to move from an open position to a closed position. In the closed position, the first clip member is disposed on top of the second clip member such that the inner surface of the first clip member and the inner surface of the second clip member define a lumen. The first clip member includes a coupling member, and the second clip member includes a coupling member. In the closed position, the coupling member of the first clip member engages the coupling member of the second clip member to assist with keeping the connector in the closed position. The coupling member of the first clip member and the coupling member of the second clip member, collectively, define a snap-fit joint connection. The hinge member includes a living hinge. The first clip member includes an outer surface, and the outer surface includes a curved portion and a planar portion. The inner connector defines a lumen. The inner surface of the first clip member includes a plurality of protrusions.

According to an aspect, a bodily implant includes a connector configured to connect a first tube member and a second tube member such that fluid can be transferred through the first tube member and the second tube member. The connector includes a first rotational connector including a lumen, and a second rotational connector including a lumen. The first rotational connector is configured to engage with the second rotational connector and to rotate with respect to the second rotational connector to couple the first rotational connector and the second rotational connector in a locked configuration. The connector includes an inner connector configured to be disposed in the lumen of the first rotational connector and the lumen of the second rotational connector.

According to some aspects, the bodily implant may include any of the following features (or any combination thereof). The first rotational connector includes a c-shaped collar, and the second rotational connector includes a c-shaped collar. The diameter of the lumen of the first rotational connector and/or the diameter of the lumen of the second rotational connector may decrease in response to rotation of the first rotational connector with respect to the second rotational connector to place the connector in a compressed configuration. The first rotational connector includes a protrusion and a connector groove, and the second rotational connector includes a protrusion and a connector groove. The protrusion of the first rotational connector is configured to be inserted into the connector groove of the second rotational connector while the protrusion of the second rotational connector is inserted into the connector groove of the first rotational connector. The protrusion of the first rotational connector is configured to move along the connector groove of the second rotational connector in response to the first rotational connector being rotated with respect to the second rotational connector.

According to an aspect, a bodily implant includes a connector configured to connect a first tube member and a second tube member such that fluid can be transferred through the first tube member and the second tube member. The connector includes a tab having an inner connector, and a clip member having a side slot, a tab slot, and a lumen. The tab configured to be inserted into the clip member via the tab slot such that the inner connector is inserted within the lumen of the clip member via the side slot.

According to some aspects, the bodily implant may include any of the following features (or any combination thereof). The clip member is a c-shaped collar. The tab is a push tab configured to push the inner connector into the lumen of the clip member. The tab is a pull tab configured to pull the inner connector into the lumen of the clip member. The inner connector includes a ferrule.

BRIEF DESCRIPTION OF THE DRAWINGS

FIG. 2B illustrates the clip connector in an open position according to an aspect.

FIG. 2C illustrates the clip connector in the open position according to another aspect.

FIG. 4A illustrates a push slide clamp connector in an unassembled state according to an aspect.

FIG. 4B illustrates the push slide clamp connector in an assembled state according to an aspect.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure. For example, in some embodiments, the patient may be a human male, a human female, or any other mammal.

Figure 1:
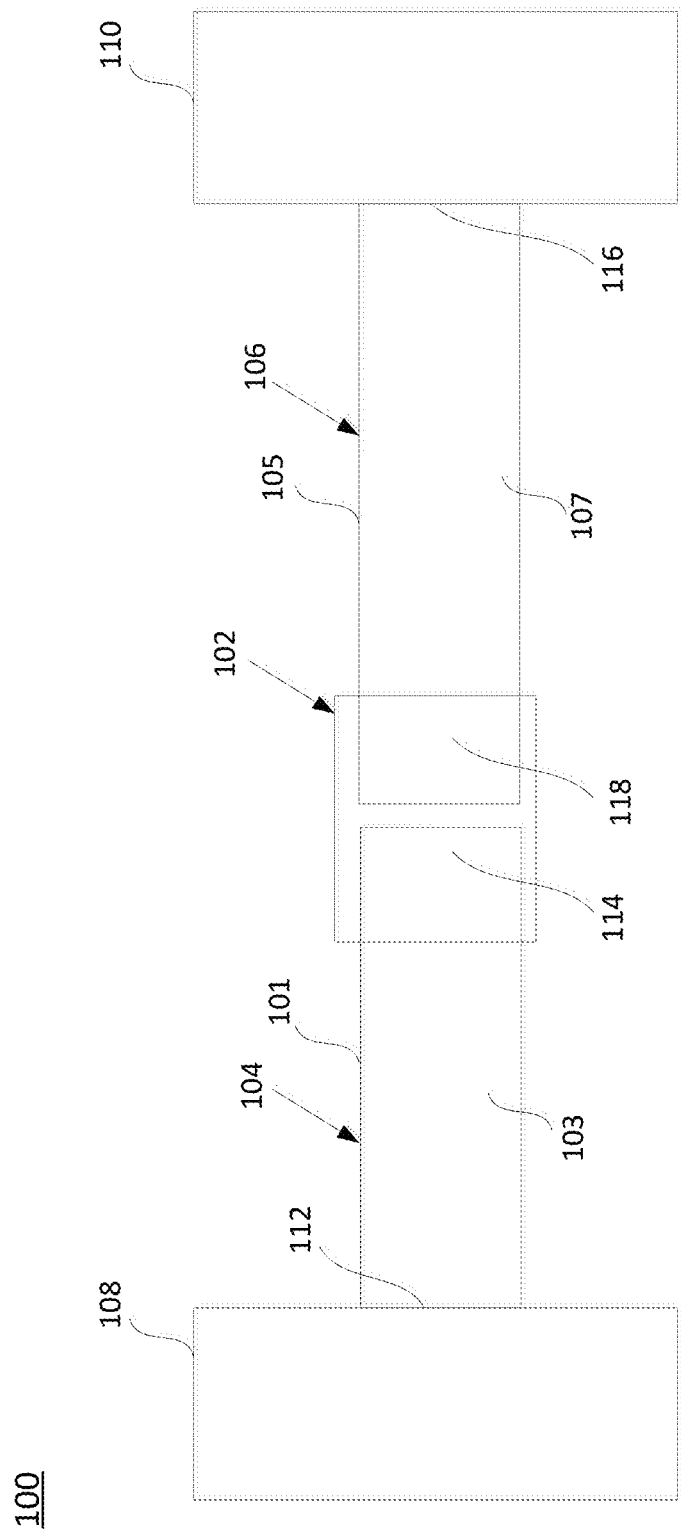
FIG. 1 schematically illustrates a bodily implant having a connector that connects a first tube member with a second tube member according to an aspect.

FIG. 1 illustrates a connector 102 that connects a first tube member 104 and a second tube member 106 of a bodily implant 100 according to an aspect. The bodily implant 100 may be any type of medical device that is implanted into a patient of a body. While at least a portion of the first tube member 104 and the second tube member 106 are disposed within the body, the connector 102 is coupled to the first tube member 104 and the second tube member 106 so that fluid can be exchanged between the first tube member 104 and the second tube member 106 during use of the bodily implant. In some examples, the bodily implant 100 includes a penile prosthesis. In some examples, the bodily implant 100 includes a urinary control system. However, the bodily implant 100 may include any type of medical device that uses tube members to transfer fluid between components of the bodily implant 100.

The first tube member 104 includes a first end portion 112 and a second end portion 114. The first tube member 104 includes a sidewall 103 defining a lumen 101. In some examples, the first tube member 104 includes Kink Resistant Tubing (KRT). The second tube member 106 includes a first end portion 116 and a second end portion 118. The second tube member 106 includes a sidewall 105 defining a lumen 107. In some examples, the second tube member 106 includes KRT.

The bodily implant 100 includes a first component 108 coupled to the first end portion 112 of the first tube member 104. The first component 108 may be any part of the bodily implant 100 that is implanted into the body of the patient. In some examples, the first component 108 includes a pump assembly having a pump bulb. In some examples, the first component 108 includes an inflatable member. In some examples, the first component 108 includes a reservoir.

The bodily implant 100 includes a second component 110 coupled to the first end portion 116 of the second tube member 106. The second component 110 may be any part of the bodily implant 100 that is implanted into the body of the patient. In some examples, the second component 110 includes a pump assembly having a pump bulb. In some examples, the second component 110 includes an inflatable member. In some examples, the second component 110 includes a reservoir.

The connector 102 is used to couple the first tube member 104 and the second tube member 106 together. For example, the connector 102 is coupled to the second end portion 114 of the first tube member 104, and the connector 102 is coupled to the second end portion 118 of the second tube member 106, such that fluid can be transferred between the first component 108 and the second component 110. In some examples, while the first tube member 104 and the second tube member 106 are disposed within the body of the patient, the first tube member 104 is connected to the second tube member 106 using the connector 102.

The connector 102 may include fewer components than conventional connectors. In some examples, the connector 102 is a single-piece. In some examples, the connector 102 is connected to the first tube member 104 and the second tube member 106 without the use of a specialized tool. In some examples, the connector 102 is connected to the first tube member 104 and the second tube member 106 by a hand of the operator (e.g., no tool is required). In some examples, an ambulatory tool (e.g., mosquito clamp) may be used to connect the connector 102 to the first tube member 104 and the second tube member 106.

FIGS. 2A through 2M illustrate a clip connector 202 according to various aspects. The clip connector 202 is an example of the connector 102 of FIG. 1.

The clip connector 202 includes a first clip member 220, a second clip member 222, and a hinge member 224. In some examples, the clip connector 202 includes a medical grade plastic material. In some examples, the first clip member 220, the second clip member 222, and the hinge member 224 are integrally formed from a single component (e.g., injection molded using a medical grade plastic material). In some examples, the first clip member 220, the second clip member 222, and the hinge member 224 are separate components and coupled together. The first clip member 220 and the second clip member 222 may move with respect to each other via the hinge member 224. In some examples, the hinge member 224 includes a living hinge. In some examples, the hinge member 224 includes a thin flexible plastic material.

The first clip member 220 includes a first end 251, and a second end 253. In some examples, the distance between the first end 251 and the second end 253 defines a length of the first clip member 220. The first clip member 220 includes a first lateral side portion 217 and a second lateral side portion 247. The second lateral side portion 247 is disposed opposite to the first lateral side portion 217.

The second clip member 222 includes a first end 255 and a second end 257. In some examples, the distance between the first end 255 and the second end 257 defines a length of the second clip member 222. In some examples, the length of the first clip member 220 is substantially the same as the length of the second clip member 222. The second clip member 222 includes a first lateral side portion 219 and a second lateral side portion 249. The second lateral side portion 249 is disposed opposite to the first lateral side portion 219. The hinge member 224 is coupled to (or extends from) the second lateral side portion 247 of the first clip member 220. The hinge member 224 is coupled to (or extends from) the second lateral side portion 249 of the second clip member 222. In some examples, the length of the hinge member 224 is substantially the same as the length of the first clip member 220 and/or the length of the second clip member 222. In some examples, the length of the hinge member 224 is less than the length of the first clip member 220 and/or the length of the second clip member 222.

The first clip member 220 includes a coupling member 240. In some examples, the coupling member 240 is defined by or extends from the first lateral side portion 217 of the first clip member 220. In some examples, the coupling member 240 extends along the entire length of the first lateral side portion 217. In some examples, the coupling member 240 extends along only a portion of the length of the first lateral side portion 217.

The second clip member 222 includes a coupling member 242 configured to be engaged with the coupling member 240 of the first clip member 220. In some examples, the coupling member 242 is defined by or extends from the first lateral side portion 219 of the second clip member 222. In some examples, the coupling member 242 extends along the entire length of the first lateral side portion 219. In some examples, the coupling member 242 extends along only a portion of the length of the first lateral side portion 219.

The coupling member 240 and the coupling member 242, collectively, define a locking mechanism. When moving from the open position to the closed position, the first clip member 220 and the second clip member 222 move towards each other. In the closed position, the first clip member 220 is disposed on top of the second clip member 222 (or vice versa). The coupling member 240 is configured to engage with the coupling member 242 in order to keep the clip connector 202 in the closed position such that the first clip member 220 and the second clip member 222 do not move apart from each other during use of the bodily implant.

In some examples, the coupling member 240 and the coupling member 242, collectively, define a snap-fit joint connection. In some examples, referring to FIG. 2F, the coupling member 240 includes a flexible member 270, and an overhang portion 272 defining a contacting edge 274. The coupling member 242 includes an overhang portion 271 defining a contacting edge 273. When moving to the closed position, the flexible member 270 may flex in order to allow the overhang portion 272 to move past the overhang portion 272. When the contacting edge 274 moves past the overhang portion 271, the flexible member 270 snaps back such that the contacting edge 274 faces the contacting edge 273. In some examples, the contacting edge 274 is disposed in a plane substantially parallel with the contacting edge 273. The engagement of the overhang portion 271 and the overhang portion 272 allows the first clip member 220 and the second clip member 222 to remain in the closed position.

The first clip member 220 includes an outer surface 223 and an inner surface 243. In some examples, the outer surface 223 includes a convex portion. In some examples, the majority of the outer surface 223 is convex. In some examples, the outer surface 223 includes a planar portion 221. The planar portion 221 may be a section of the outer surface 223 that is planar (e.g., devoid of a curvature). In some examples, the inner surface 243 includes a convex portion. In some examples, the majority of the inner surface 243 is convex. In some examples, the inner surface 243 of the first clip member 220 is smooth. In some examples, the inner surface of the first clip member 220 includes a surface feature 241. In some examples, the surface feature 241 includes cross-hatching. Cross-hatching may promote connector tubing connection strength (tensile). In some examples, referring to FIG. 2J, the surface feature 241 may include protrusions 282 that extend from the inner surface 243. The protrusions 282 may also promote connector tubing connection strength (tensile).

Figure 2A:
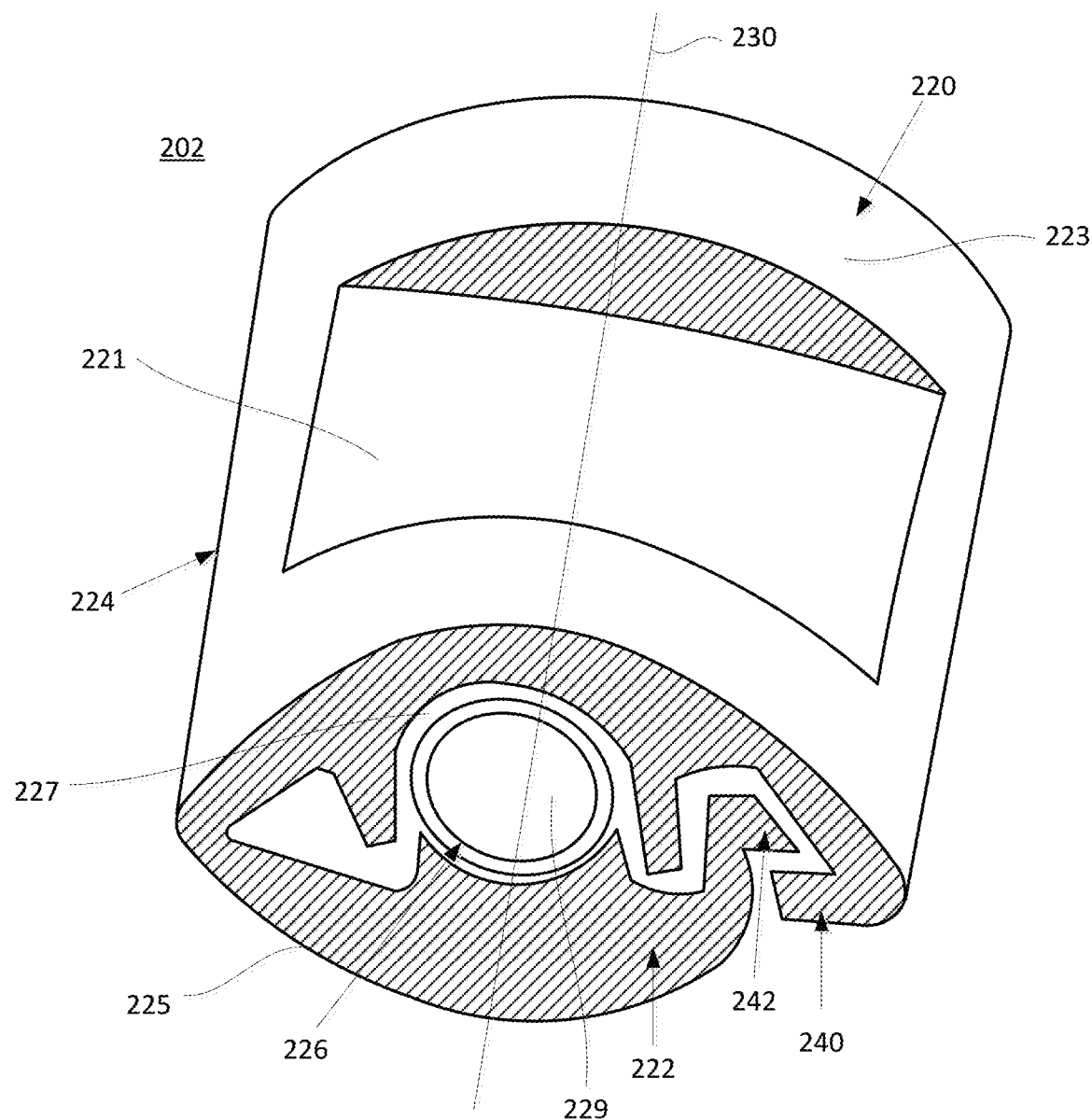
FIG. 2A illustrates a clip connector in a closed position according to an aspect.
Figure 2D:
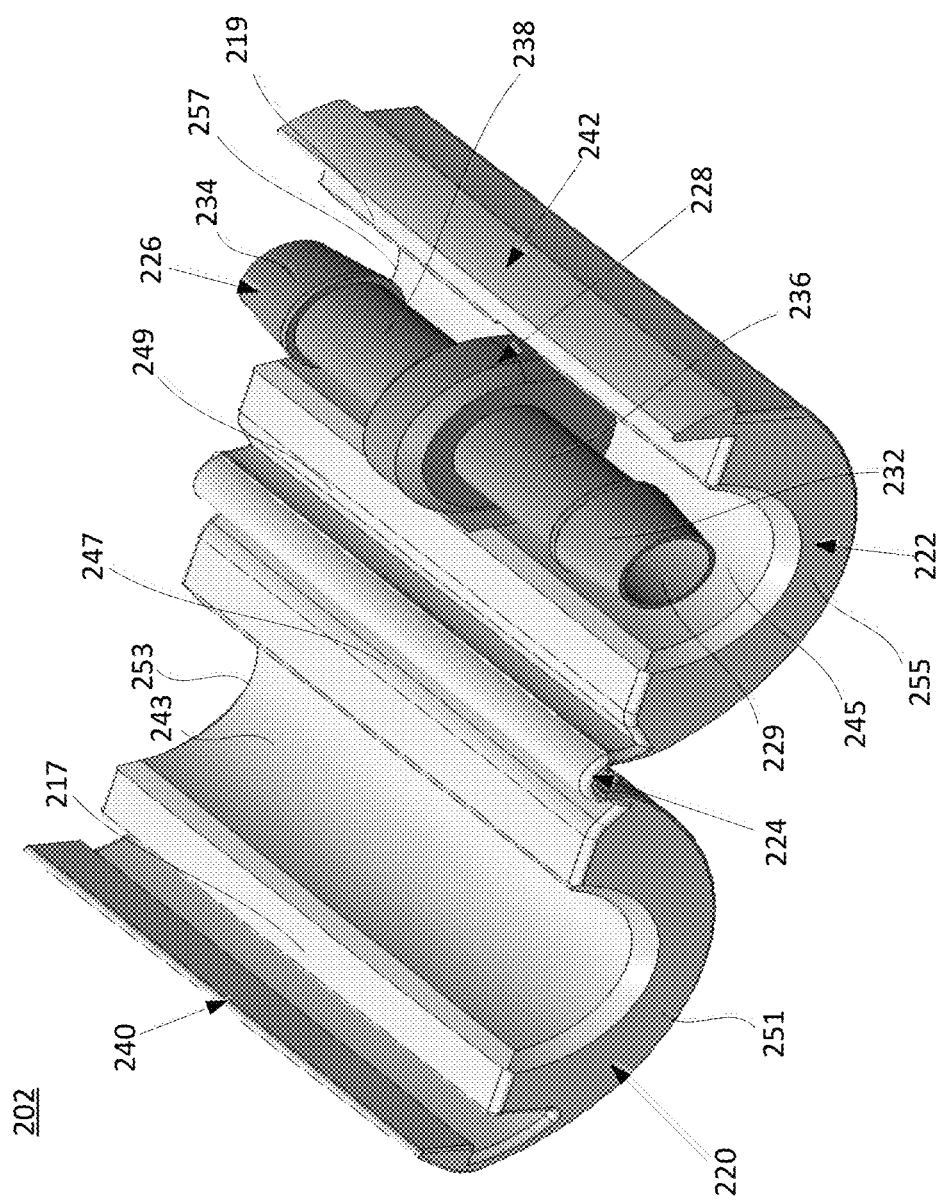
FIG. 2D illustrates the clip connector in the open position according to another aspect.
Figure 2E:
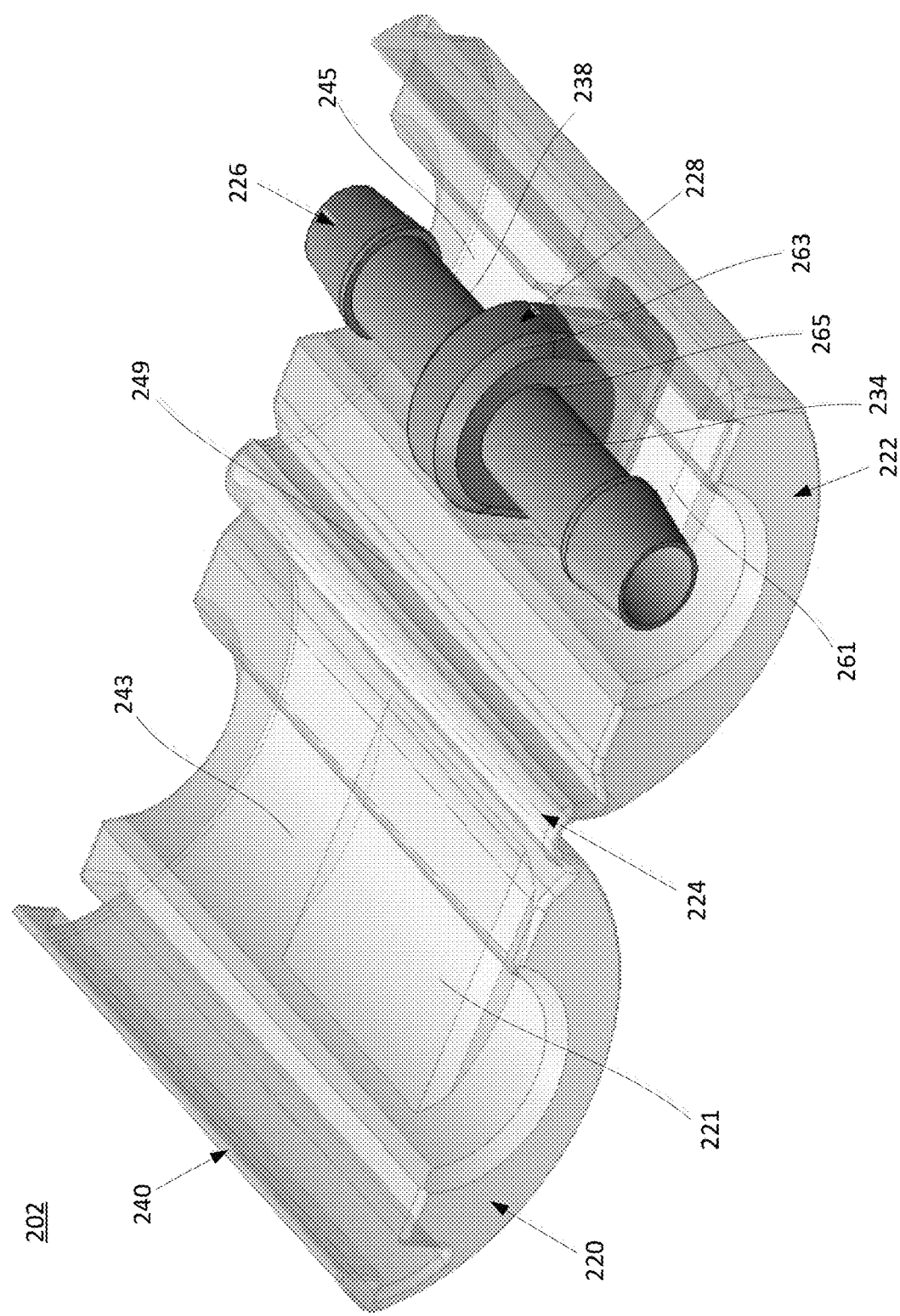
FIG. 2E illustrates a transparent perspective of the clip connector in the open position according to another aspect.
Figure 2F:
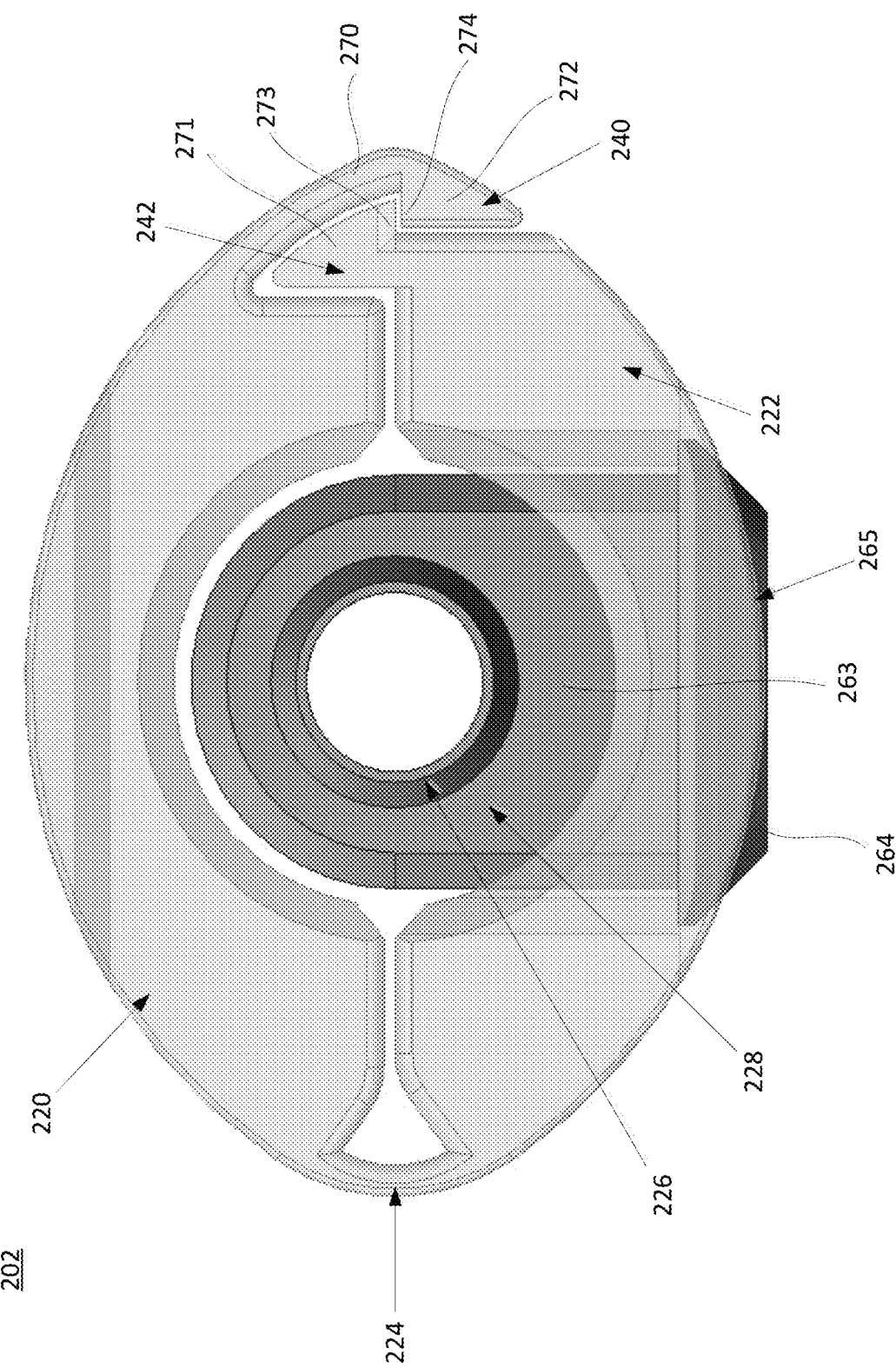
FIG. 2F illustrates a perspective of the clip connector with a retaining member and a locking mechanism according to an aspect.
Figure 2G:
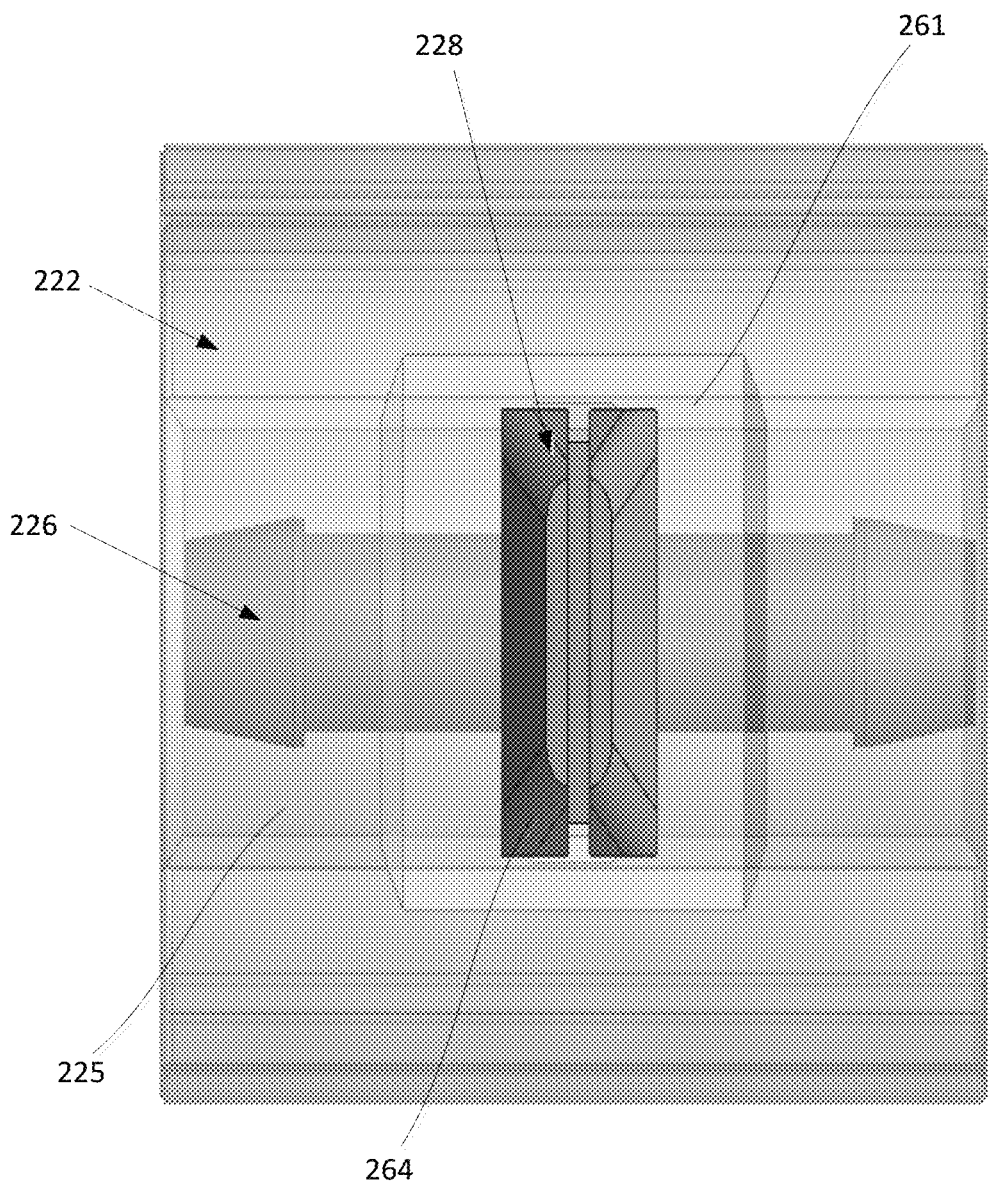
FIG. 2G illustrates an inner connector and the retaining member of the clip connector according to an aspect.
Figure 2H:
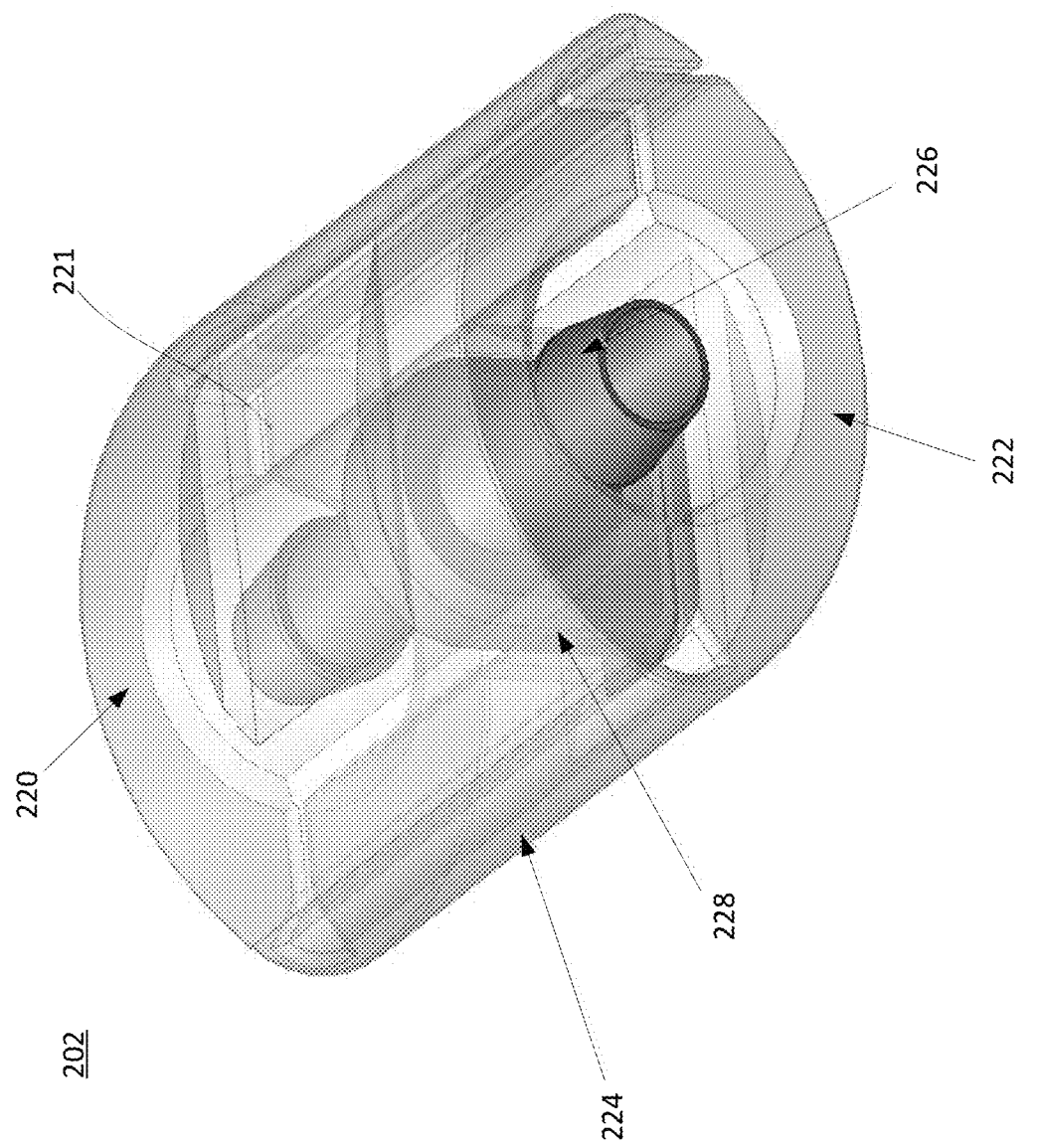
FIG. 2H illustrates the clip connector according to another aspect.
Figure 2I:
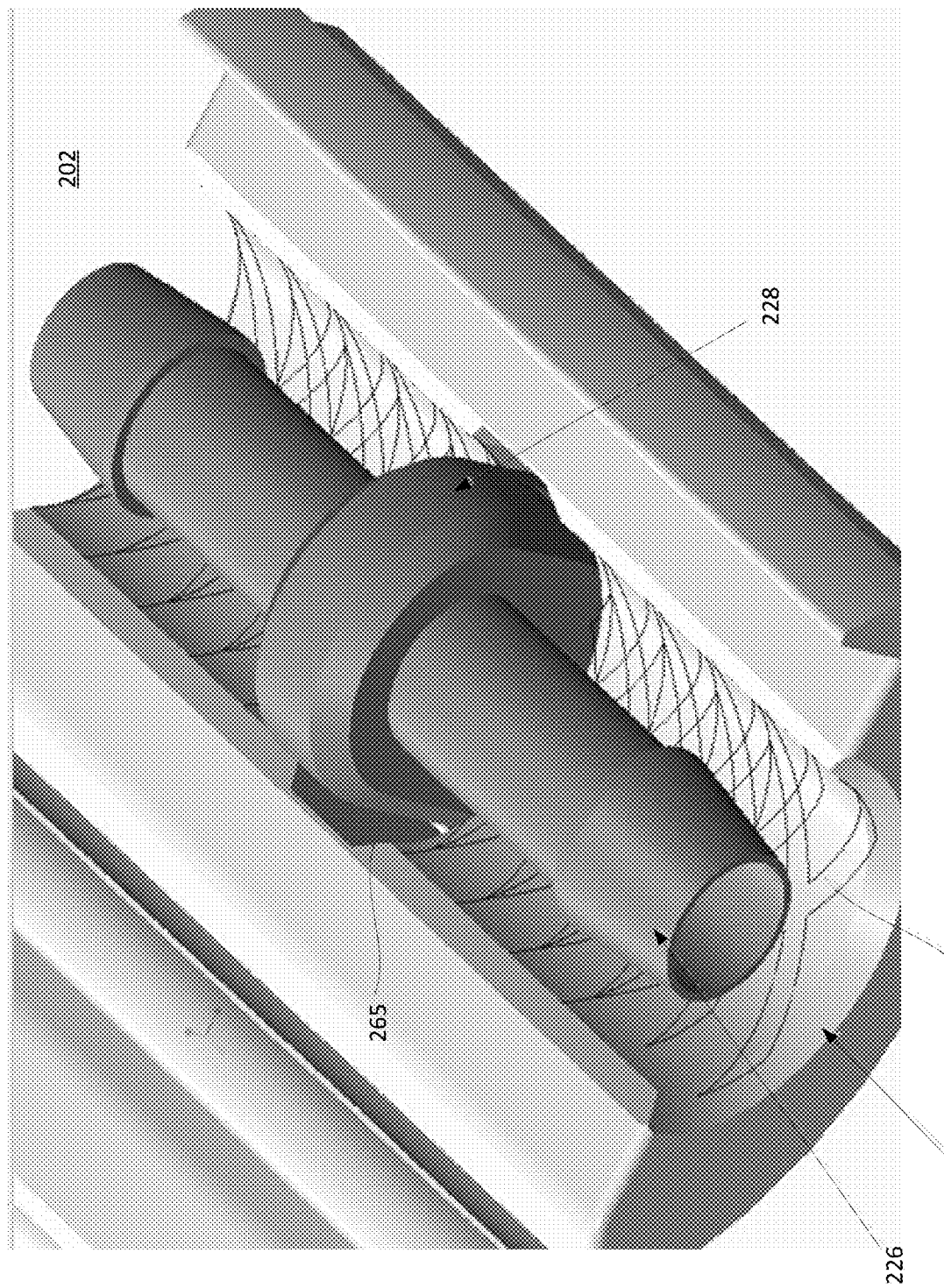
FIG. 2I illustrates an inner surface of the clip connector having a surface feature according to an aspect.
Figure 2J:
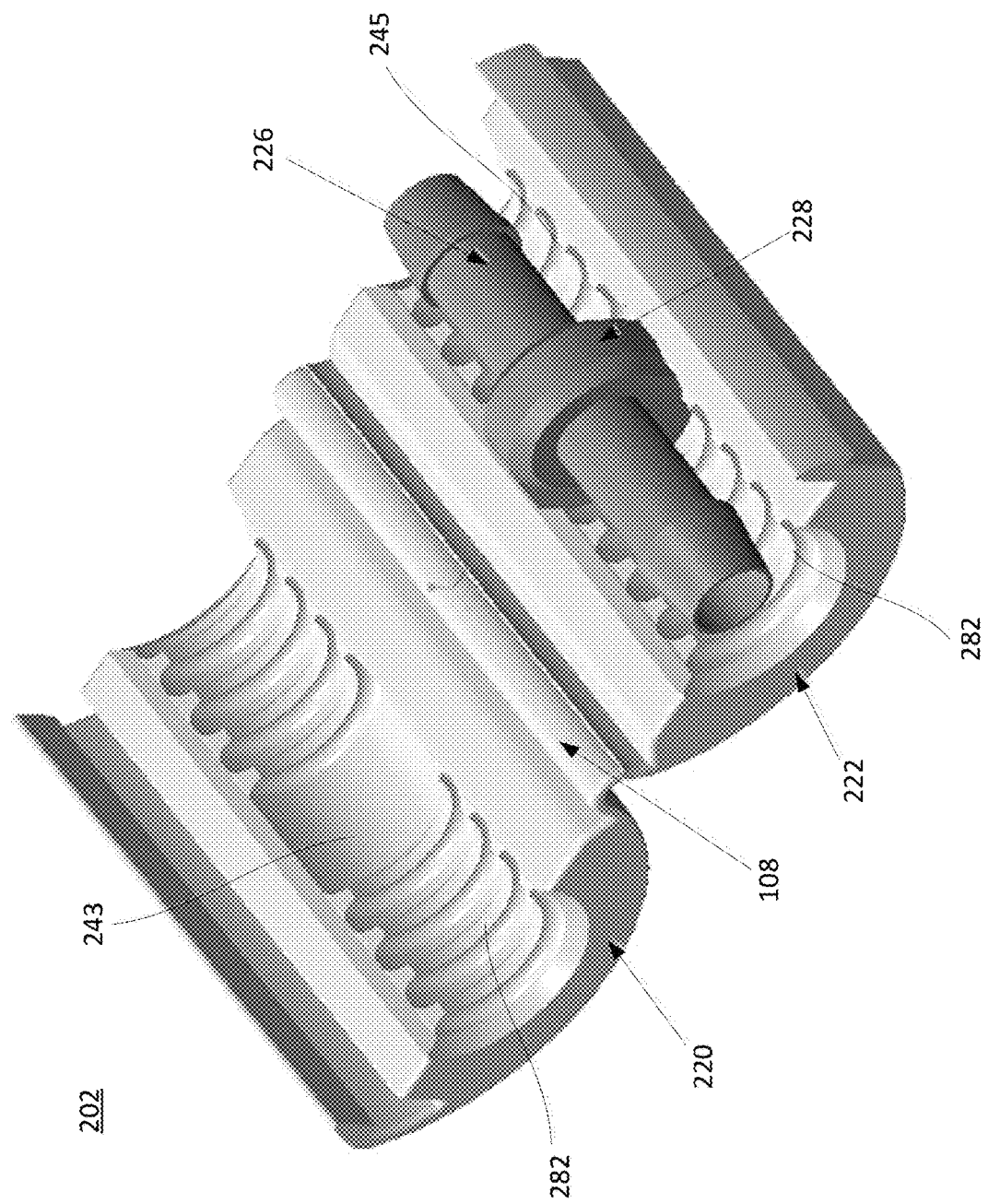
FIG. 2J illustrates the clip connector having protrusions on an inner surface of a clip member according to an aspect.
Figure 2K:
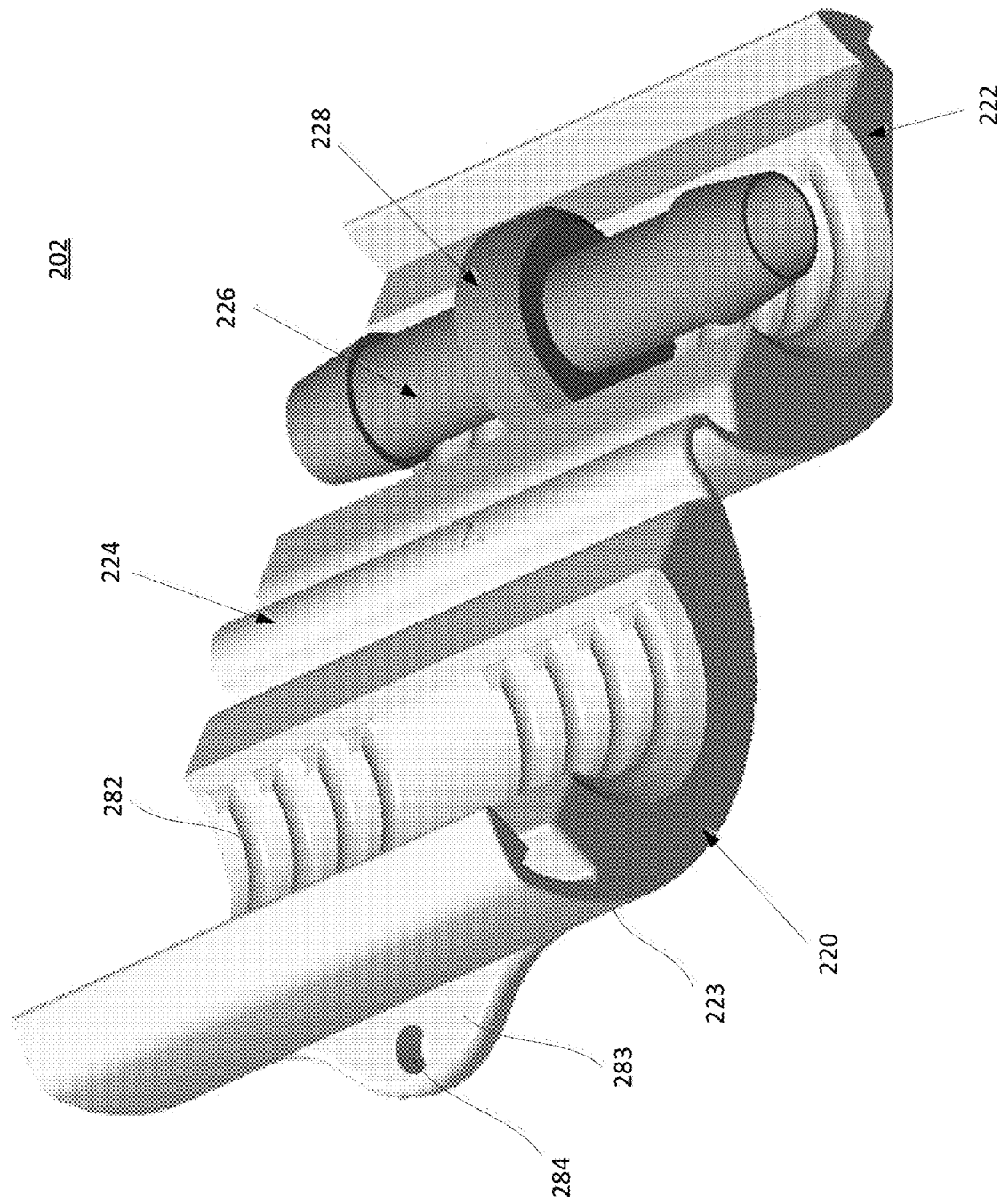
FIG. 2K illustrates the clip connector having a suture connection tab according to an aspect.
Figure 2L:
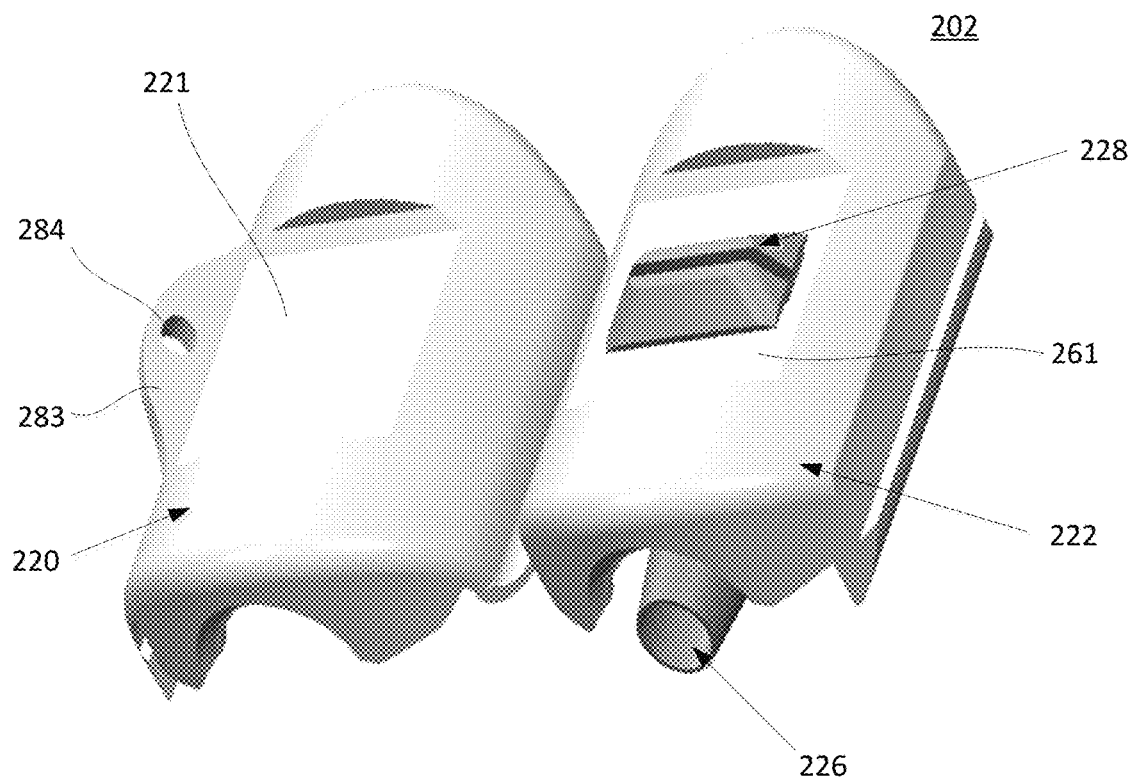
FIG. 2L illustrates the clip connector according to another aspect.
Figure 2M:
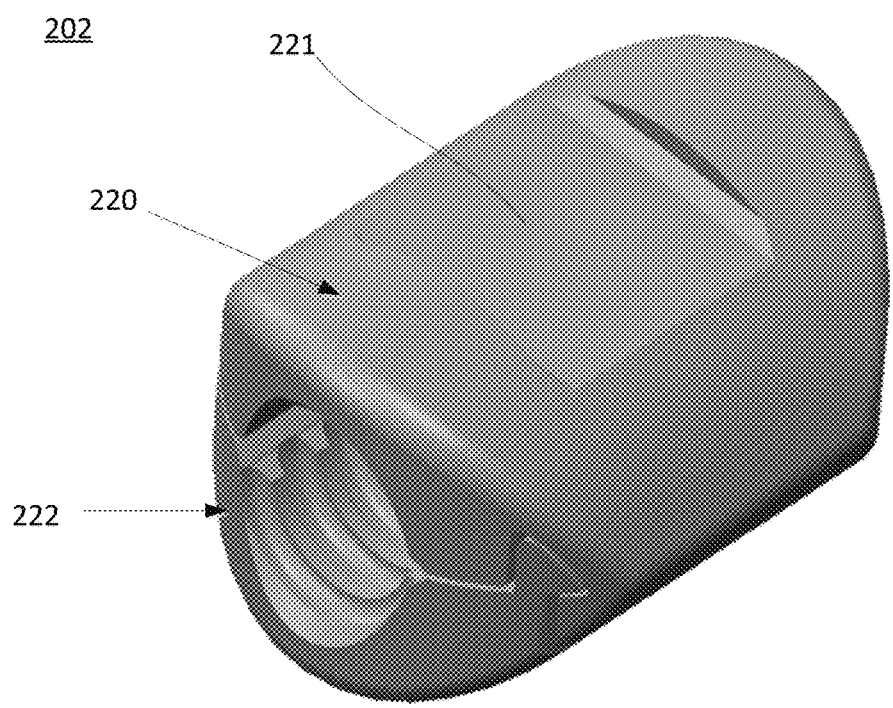
FIG. 2M illustrates the clip connector according to another aspect.

In some examples, referring to FIG. 2K, the first clip member 220 includes a suture connection tab 283 that defines an opening 284. A suture (not shown) may be coupled to the suture connection tab 283 via the opening 284. The suture connection tab 283 may extend from the outer surface 223 of the first clip member 220.

The second clip member 222 includes an outer surface 225 and an inner surface 245. In some examples, the outer surface 225 includes a convex portion. In some examples, the majority of the outer surface 225 is convex. In some examples, the outer surface 225 includes a planar portion 261. For example, the planar portion 261 of the outer surface 225 may be a section of the outer surface 225 that is planar (e.g., devoid of a curvature). In some examples, the inner surface 245 includes a convex portion. In some examples, the majority of the inner surface 245 is convex. In some examples, the inner surface 245 is smooth. In some examples, the inner surface 245 includes a surface feature 241. In some examples, referring to FIG. 2I, the surface feature 241 may include cross-hatching 280. In some examples, referring to FIG. 2J, the surface feature 241 may include protrusions 282 that extend from the inner surface 245.

In some examples, a tool is used to contact the planar portion 221 of the first clip member 220 and the planar portion 261 of the second clip member 222 in order to close the clip connector 202 such that the coupling member 240 engages with the coupling member 242 to place the clip connector 202 in the closed position.

In the closed position (as shown in FIG. 2A), the clip connector 202 defines a lumen 227 along a longitudinal axis 230 of the clip connector 202. The lumen 227 is formed by the inner surface 243 of the first clip member 220 and the inner surface 245 of the second clip member 222. For example, the inner surface 243 defines one part of the lumen 227 and the inner surface 245 defines the other part of the lumen 227. In some examples, the lumen 227 has a circular shape. In some examples, the clip connector 202 defines a cylindrical shape where the first clip member 220 defines one half of the cylinder and the second clip member 222 defines the other half of the cylinder. In some examples, the clip connector 202 has a rectangular shape. In some examples, referring to FIGS. 2L and 2M, the clip connector 202 has a pill-type shape.

The clip connector 202 includes an inner connector 226 disposed within the lumen 227. The inner connector 226 defines a lumen 229. In some examples, the inner connector 226 is a tubular member. In some examples, the inner connector 226 includes a ferrule. Referring to FIG. 2B, the inner connector 226 includes a first end portion 232, a second end portion 234, a shaft portion 236, and a shaft portion 238. In some examples, the first end portion 232 is a barbed portion. In some examples, the first end portion 232 includes an enlarged portion. In some examples, the first end portion 232 has a size (e.g., diameter) larger than a size of the shaft portion 236 (and a size of the shaft portion 238). In some examples, the second end portion 234 is a barbed portion. In some examples, the second end portion 234 is an enlarged portion. In some examples, the second end portion 234 has a size larger than the size of the shaft portion 238.

The clip connector 202 includes a retaining member 228. The retaining member 228 is configured to hold the inner connector 226 on an inside of the clip connector 202. The retaining member 228 may include a retaining body 263 defining an opening 265. The inner connector 226 extends through the opening 265 such that the shaft portion 236 is disposed on one side of the retaining body 263 and the shaft portion 238 is disposed on the other side of the retaining body 263. The opening 265 may have a diameter that is slighter larger than a diameter of the inner connector 226 at the central region of the inner connector 226. In some examples, the diameter of the opening 265 may be smaller than one of the diameters of the first end portion 232 of the inner connector 226. In some examples, the diameter of the opening 265 may be smaller than one of the diameters of the second end portion 234 of the inner connector 226.

In some examples, the retaining member 228 is coupled to (or disposed on) the inner surface 243 of the first clip member 220. In some examples, the retaining member 228 is coupled to (or disposed on) to the inner surface 245 of the second clip member 222. In some examples, in the open state, the retaining member 228 holds but allows the inner connector 226 to move through the opening 265 of the retaining member 228 (e.g., free floating in the clip connector 202). However, when the clip connector 202 is move to the closed state, the inner connector 226 is locked into place (e.g., prevented from moving through the opening 265 of the retaining member 228).

In some examples, the retaining member 228 is a ferrule retaining clip. For example, referring to FIGS. 2F and 2G, the retaining member 228 may be clipped into the second clip member 222. For example, the second clip member 222 may define an opening 265, and the retaining body 263 may be inserted into the opening 265 (from the inner surface 245 until a portion 264 of the retaining body 263 extends through the outer surface 225 of the second clip member 222. The portion 264 may define a coupling feature such that the retaining body 263 remains coupled to the second clip member 222.

In the open position (as shown in FIGS. 2B-2C), the first clip member 220 is disposed part from the second clip member 222. Then, an operator places an end portion 214 of a first tube member 204 over a portion of the inner connector 226. For example, the end portion 214 of the tube member is disposed on the shaft portion 236 of the inner connector 226. An operator places an end portion 218 of a second tube member 206 over a portion of the inner connector 226. For example, the end portion 218 is disposed on the shaft portion 238 of the inner connector 226. Then, the first clip member 220 and the second clip member 222 are moved towards each other until the coupling member 240 engages with the coupling member 242 to place the clip connector 202 in the closed position. In the closed position, the first end portion 232 of the inner connector 226 and the inner surfaces 243, 245 compress a portion of the first tube member 204, and the second end portion 234 of the inner connector 226 and the inner surfaces 243, 245 compress a portion of the second tube member 206. In some examples, in the closed position, the protrusions 282 and the shaft portion 236 compress the end portion 214 of the first tube member 204, and the protrusions 282 and the shaft portion 238 compress the end portion 218 of the second tube member 206.

FIGS. 3A through 3G illustrate a rotational connector 302 according to various aspects. The rotational connector 302 is an example of the connector 102 of FIG. 1. The rotational connector 302 may be assembled to connect tube members without using equipment. For example, the rotational connector 302 may be assembled using the hand of the operator. The rotational connector 302 includes a first rotational connector 320 and a second rotational connector 322

Figure 3A:
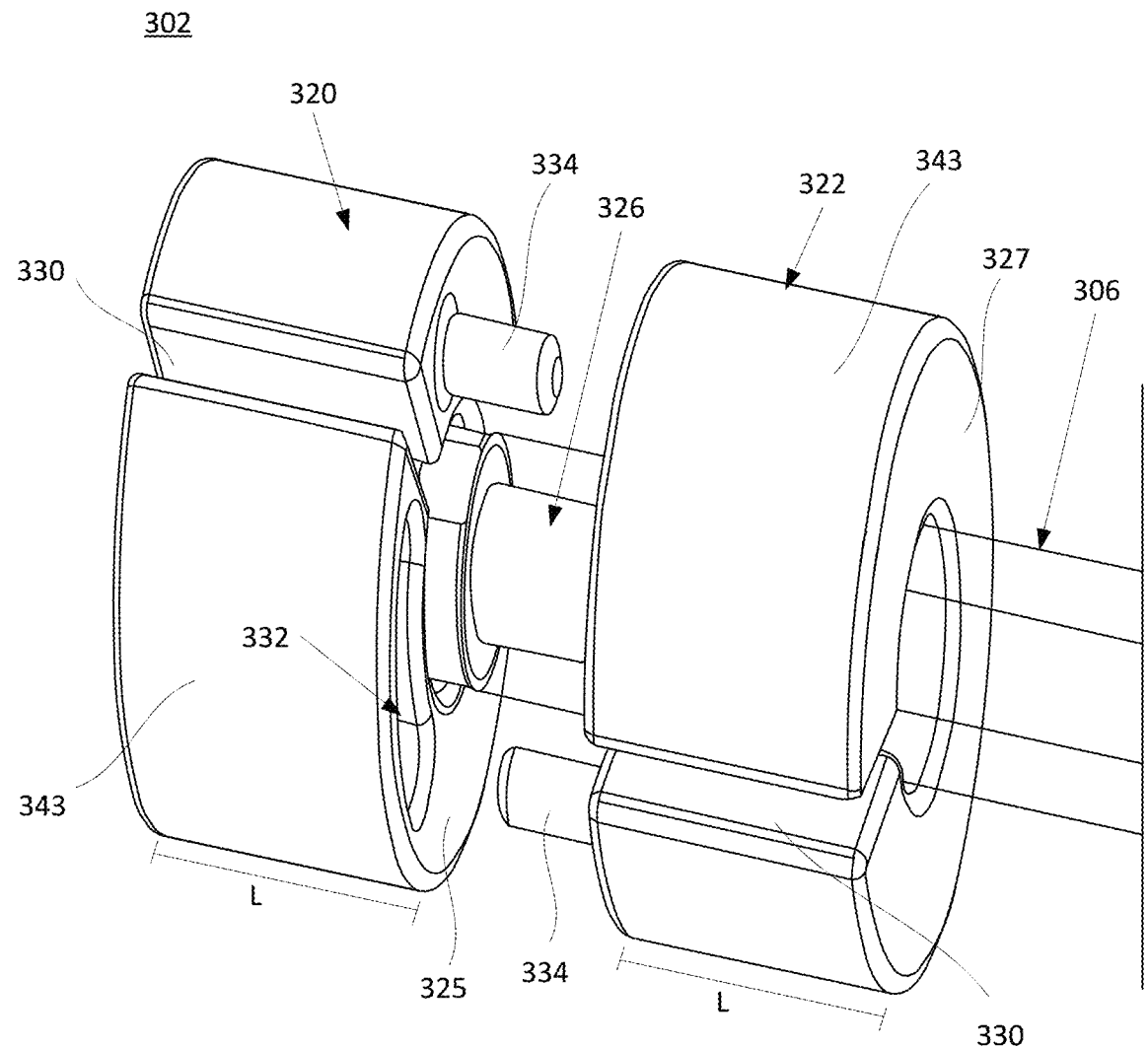
FIG. 3A illustrates a rotational connector according to an aspect.
Figure 3B:
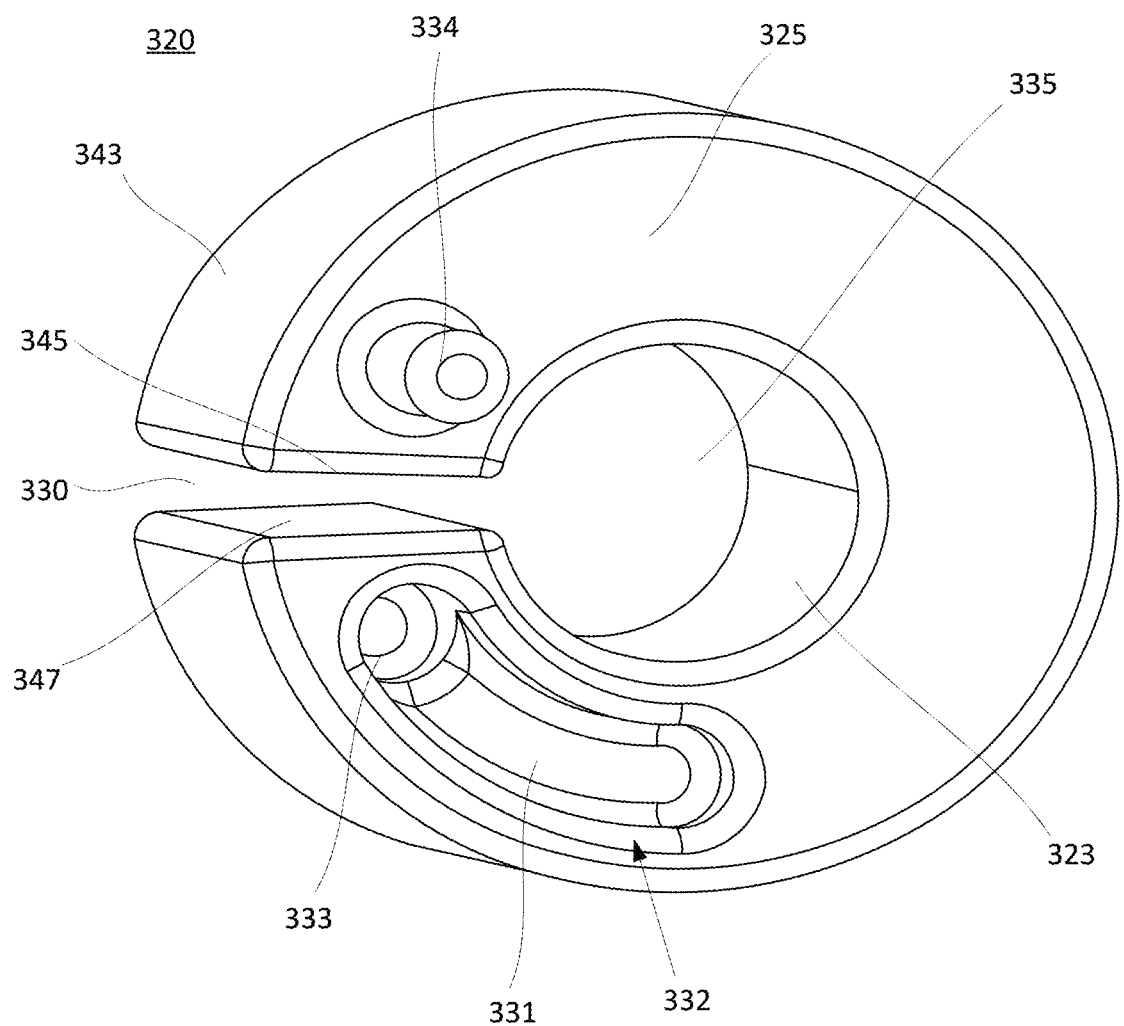
FIG. 3B illustrates a first rotational connector of the rotational connector according to an aspect.
Figure 3C:
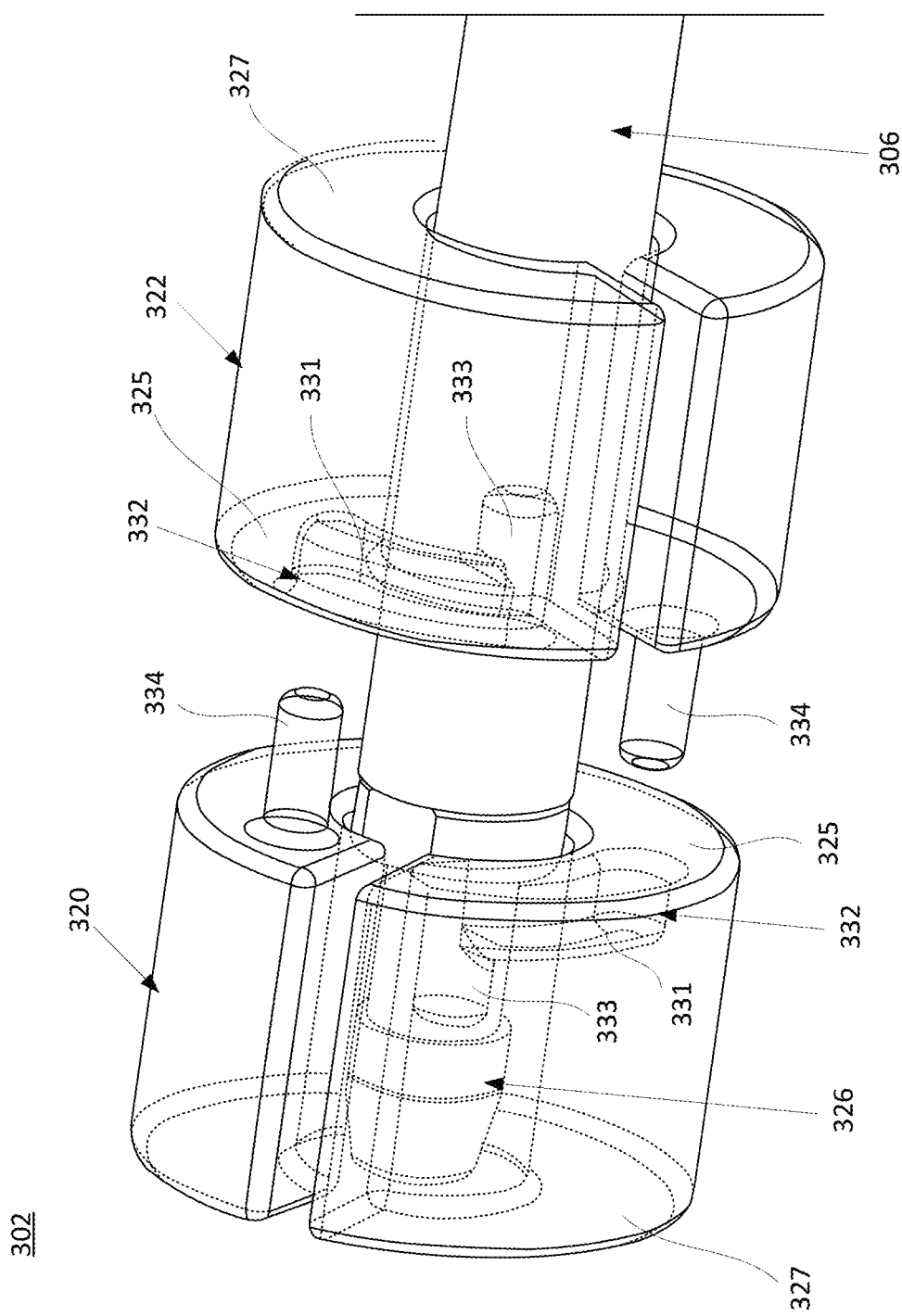
FIG. 3C illustrates the rotational connector according to another aspect.

Referring to FIGS. 3A-3C, the first rotational connector 320 contacts the second rotational connector 322 (such that their mating features align), and the first rotational connector 320 rotates with respect to the second rotational connector 322 (or vice versa), which completes a locking mechanism that couples the first rotational connector 320 and the second rotational connector 322 together. In some examples, the locking mechanism is irreversible (e.g., the first rotational connector 320 cannot become separated from the second rotational connector 322 without damaging the rotational connector 302). In some examples, the locking mechanism is reversible (e.g., upon application of a greater rotational force in the opposite direction). In some examples, the rotation is a quarter turn. In some examples, the first rotational connector 320 is the same as the second rotational connector 322. In some examples, the second rotational connector 322 has one or more features than are different or addition to the first rotational connector 320. The following disclosure further describes the first rotational connector 320. It is noted that the second rotational connector 322 has the same features of the first rotational connector 320, and therefore a detailed description of the second rotational connector 322 is omitted for the sake of brevity.

In some examples, the first rotational connector 320 is a c-shaped collar. The first rotational connector 320 includes an interface surface 325 and a back surface 327. The interface surface 325 and the back surface 327 may be separated by a length (L) of the first rotational connector 320. In some examples, the interface surface 325 is disposed in a plane that is parallel to a plane of the back surface 327. The first rotational connector 320 includes an inner surface 323 and an outer surface 343. The inner surface 323 is curved. The distance between the inner surface 323 and the outer surface 343 may define a size of the first rotational connector 320. In some examples, the size is the same (or uniform) around the first rotational connector 320. In some examples, the distance may vary (or be different) between the inner surface 323 and the outer surface 343 at different locations around the first rotational connector 320. The inner surface 323 may define an inner diameter of the first rotational connector 320. In some examples, the entire inner surface 323 is curved. The inner surface 323 extends from the interface surface 325 to the back surface 327. The inner surface 323 defines a lumen 335 along a central axis of the first rotational connector 320. The outer surface 343 is curved. In some examples, the entire outer surface 343 is curved. The outer surface 343 extends from the interface surface 325 to the back surface 327. The outer surface 343 may define an outer diameter of the first rotational connector 320. In some examples, the curvature of the outer surface 343 may substantially correspond to the curvature of the inner surface 323.

The first rotational connector 320 defines a side slot 330. The side slot 330 may be a cutout section of the first rotational connector 320. The side slot 330 extends from the outer surface 343 to the inner surface 323. For instance, a tube member may be placed into the lumen 335 via the side slot 330. The side slot 330 defines a first surface 345 and a second surface 347. The second surface 347 may face the first surface 345. In some examples, the second surface 347 is parallel to the first surface 345. In some examples, the first surface 345 and the second surface 347 are disposed at an angle with respect to each other.

The first rotational connector 320 includes a protrusion 334, and a connector groove 332. The protrusion 334 extends from the interface surface 325. In some examples, the protrusion 334 extends from the interface surface 325 at a location that is proximate (e.g., close to) the first surface 345. In some examples, the protrusion 334 is linear. In some examples, the protrusion 334 is cylindrical elongated member. In some examples, the protrusion 334 extends in a direction that is orthogonal to the interface surface 325. In some examples, the protrusion 334 includes mating features that are configured to interface with mating features of the connector groove 332 of the second rotational connector 322 when the protrusion 334 of the first rotational connector 320 is inserted into and rotated within the connector groove 332 of the second rotational connector 322. In some examples, the protrusion 334 is a male threaded protrusion.

Figure 3D:
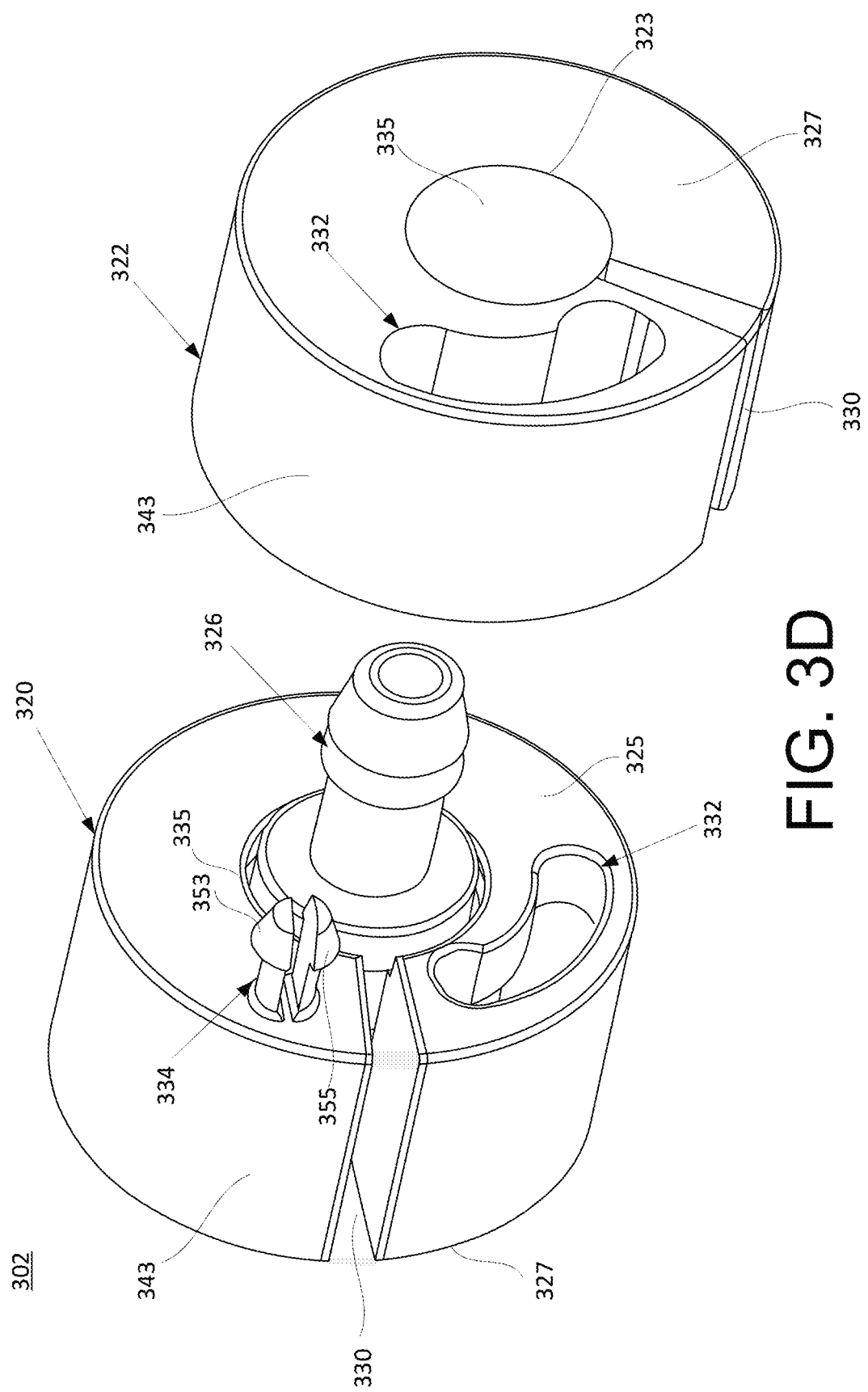
FIG. 3D illustrates the rotational connector according to another aspect.
Figure 3E:
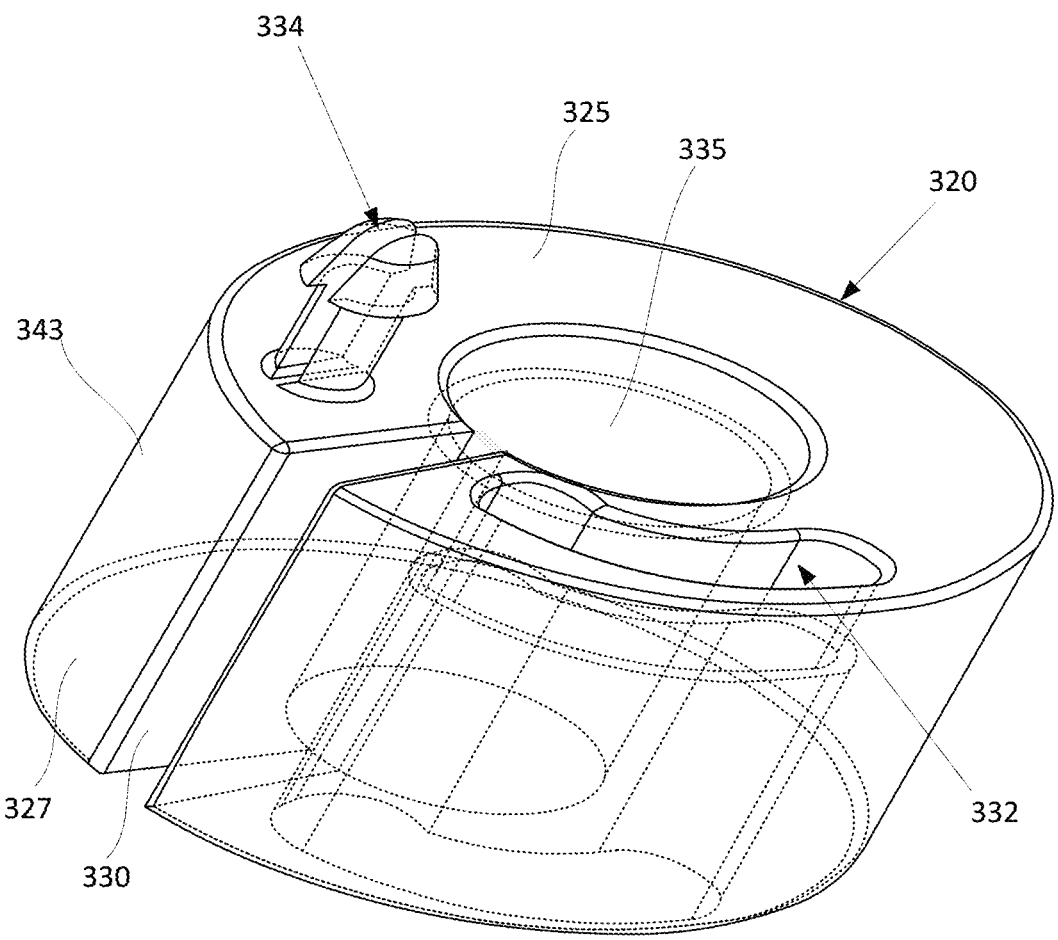
FIG. 3E illustrates a first rotational connector of the rotational connector according to an aspect.

In some examples, referring to FIGS. 3D-3E, the protrusion 334 includes a barbed fitting. In some examples, the protrusion 334 of the first rotational connector 320 (and the second rotational connector 322) includes a first flexible member 353 and a second flexible member 355. The first flexible member 353 and the second flexible member 355 are configured to move (or flex) towards each other in order to fit within the connector groove 332. Each of the first flexible member 353 and the second flexible member 355 includes an enlarged portion (or barbed portion) located at the end of its length. The second flexible member 355 may be same as the first flexible member 353. The first flexible member 353 extends from the interface surface 325, and the second flexible member 355 extends from the interface surface 325.

In some examples, as referring to FIGS. 3D-3E, the rotational connector 302 may be pre-assembled prior to the end user making the tubing connections and compressing the tube members onto the fittings. For example, the first flexible member 353 and the second flexible member 355 is pressed into connector groove 332 until the mating edges of the protrusion 334 reach the first depth, constraining the center portion of the protrusion 334. With the first rotational connector 320 and the second rotational connector 322 in the uncompressed state, the end user is able to make the tubing connections and a final rotation along the non-concentric pathway within the connector groove 332 pulls the first surface 345 and the second surface 347 together to compress the tube members. Then, the protrusion 334 locks into place within the connector groove 332. The compressive load acting on the first rotational connector 320 and the second rotational connector 322 will keep the protrusion 334 in the locked position.

The connector groove 332 is defined on the interface surface 325. The connector groove 332 may be disposed on the interface surface 325 between the inner surface 323 and the outer surface 343. In some examples, the connector groove 332 is defined on the interface surface 325 at a location proximate to the second surface 347. In some examples, the connector groove 332 has a length that is larger than its width. In some examples, as shown in FIGS. 3A-3C, the connector groove 332 has a depth smaller than the length of the first rotational connector 320. For example, the depth of the connector groove 332 may be measured from the interface surface 325 to the bottom portion of the connector groove 332.

In some examples, as shown in FIGS. 3A-3C, the connector groove 332 includes a first portion 331 having a first depth, and a second portion 333 having a second depth. The second depth may be larger than the first depth. The connector groove 332 includes mating features configured to mate with the matting features of the protrusion 334 of the second rotational connector 322 when the protrusion 334 of the second rotational connector 322 is inserted into and rotated in the connector groove 332 of the first rotational connector 320. In some examples, the connector groove 332 of the first rotational connector 320 is threaded to mate with the threads of the protrusion 334 of the second rotational connector 322. In some examples, as shown in FIGS. 3D-3E, the connector groove 332 extends from the interface surface 325 to the back surface 327. In other words, the connector groove 332 extends the entire length of the first rotational connector 320 or the second rotational connector 322.

Figure 3F:
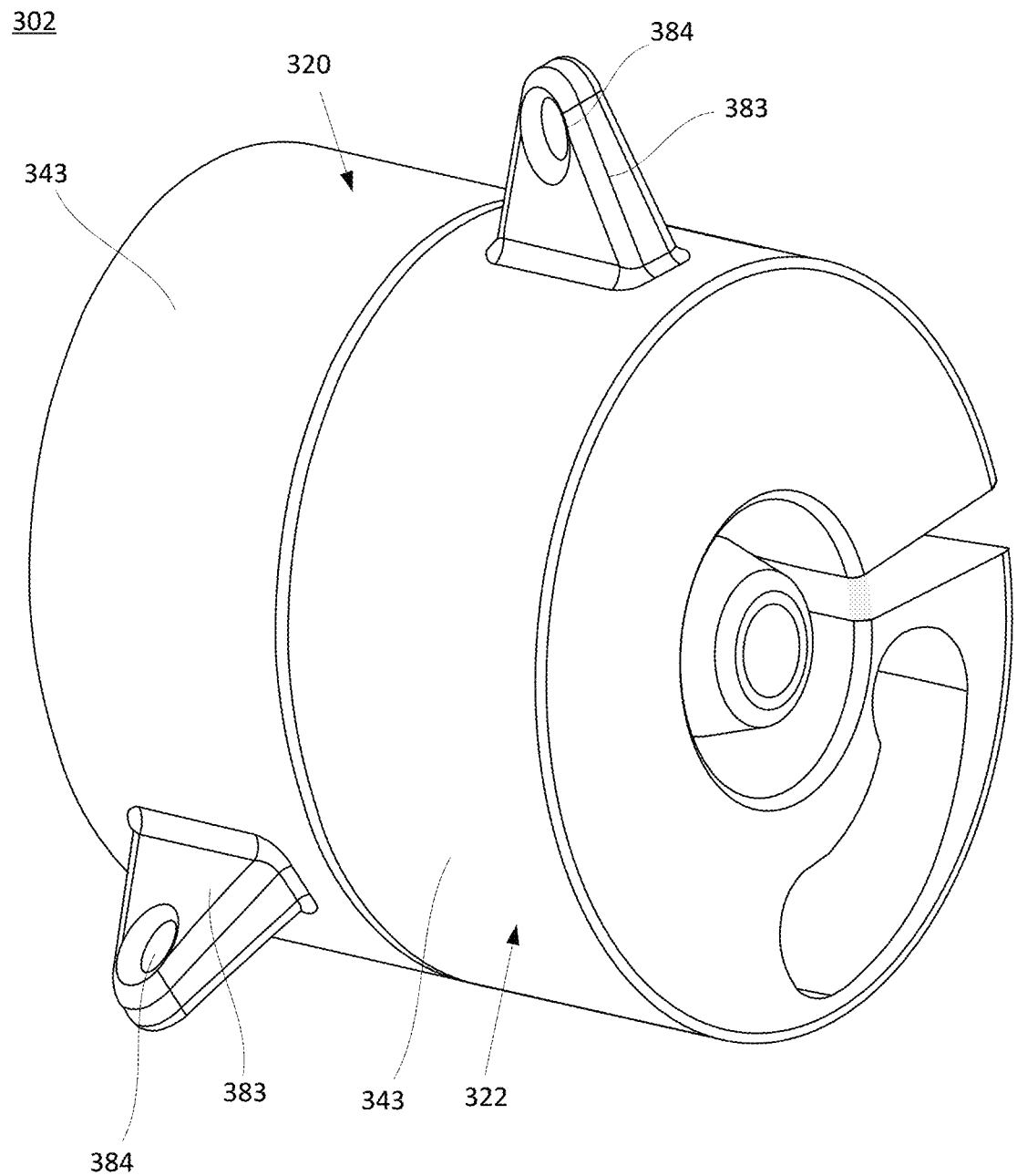
FIG. 3F illustrates the rotational connector having a suture connection tab according to an aspect.

In some examples, as shown in FIG. 3F, each of the first rotational connector 320 and the second rotational connector 322 includes a suture connection tab 383 that defines an opening 384. A suture (not shown) may be coupled to the suture connection tab 383 via the opening 384. The suture connection tab 383 may extend from the outer surface 343.

The rotational connector 302 is used to connect a first tube member (not shown in FIGS. 3A and 3C) and a second tube member 306. The first tube member may include any of the features described with reference to the first tube member 104 of FIG. 1. The second tube member 306 may include any of the features described with reference to the second tube member 106 of FIG. 1. An inner connector 326 is disposed within an end portion of the first tube member (not shown in FIGS. 3A and 3C) and within an end portion of the second tube member 306. The inner connector 326 may include any of the features discussed with reference to the inner connector 226 of FIGS. 2A through 2M. The end portion of the first tube member is inserted into the lumen 335 of the first rotational connector 320, and the end portion of the second tube member 306 is inserted into the lumen 335 of the second rotational connector 322.

The operator may move and align the interface surface 325 of the first rotational connector 320 and the interface surface 325 of the second rotational connector 322 such that the protrusion 334 of the first rotational connector 320 is inserted into the first portion 331 of the connector groove 332 of the second rotational connector 322 while the protrusion 334 of the second rotational connector 322 is inserted into the first portion 331 of the connector groove 332 of the first rotational connector 320. The operator may rotate the first rotational connector 320 with respect to the second rotational connector 322 such that the protrusion 334 of the first rotational connector 320 travels within and along the first portion 331 of the connector groove 332 of the second rotational connector 322 while the protrusion 334 of the second rotational connector 322 travels within and along the first portion 331 of the connector groove 332 of the first rotational connector 320. The operator may continue to rotate until the protrusion 334 of the first rotational connector 320 enters the second portion 333 of the connector groove 332 of the second rotational connector 322 and the protrusion 334 of the second rotational connector 322 enters the second portion 333 of the connector groove 332 of the first rotational connector 320.

In some examples, as the first rotational connector 320 rotates with respect to the second rotational connector 322, the diameter of the lumen 335 of the first rotational connector 320 and the diameter of the lumen 335 of the second rotational connector 322 decreases in order to place the rotational connector 302 in a compressed state in which the tube members are compressed against the inner connector 326 (e.g., the first surface 345 and the second surface 347 contact each other or are disposed proximate to each other). In some examples, the arc of the connector groove 332 is a smaller radius with respect to the center of the lumen 335 (non-concentric to the inner surface 323 and the outer surface 343) such that as the first rotational connector 320 and the second rotational connector 322 are rotated, the size of the lumen 335 decreases to compress the second tube member 306 onto the inner connector 326.

FIG. 4A illustrates a perspective of a push slide clamp connector 402 in an unassembled state according to an aspect. FIG. 4B illustrates a perspective of the push slide clamp connector 402 in an assembled state according to aspect. The push slide clamp connector 402 is an example of the connector 102 of FIG. 1. The push slide clamp connector 402 includes a push tab 420 integrated with an inner connector 426 (e.g., a ferrule) that is configured to be pushed into a clip connector 422 in order to couple two tube members together.

The push tab 420 includes the inner connector 426. In some examples, the inner connector 426 is coupled to the push tab 420. The inner connector 426 may include any of the features discussed with reference to the inner connector 226 of FIGS. 2A through 2M. In some examples, the inner connector 426 is orthogonal to the push tab 420. In some examples, the clip connector 422 is a c-shaped connector or collar. The clip connector 422 includes an inner surface 423 and an outer surface 443. The inner surface 423 is curved. The inner surface 423 may define an inner diameter of the clip connector 422. The inner surface 423 defines a lumen 435 along a central axis of the clip connector 422. The outer surface 443 is curved. The outer surface 443 may define an outer diameter of the clip connector 422.

The clip connector 422 defines a side slot 430. The side slot 430 may be a cutout section of the clip connector 422. The side slot 430 extends from the outer surface 443 to the inner surface 423 at a section of the clip connector 422. The side slot 430 defines a first surface 445 and a second surface 447. In some examples, the first surface 445 and the second surface 447 are disposed at an angle with respect to each other such that the side slot 430 is larger towards the outer surface 443. In some examples, the distance between the first surface 445 and the second surface 447 at the inner surface 423 is smaller than a diameter of the inner connector 426 (e.g., smaller than the enlarged ends of the inner connector 426) such that the clip connector 422 expands when the inner connector 426 is inserted into the lumen 435. In some examples, the distance between the first surface 445 and the second surface 447 at the outer surface 443 is larger than the diameter of the inner connector 426 (e.g., larger than the enlarged ends of the inner connector 426).

The clip connector 422 defines a tab slot 410 configured to receive portions of the push tab 420. In some examples, the tab slot 410 may have a thickness larger than a thickness of the push tab 420, and a length greater than the length of the push tab 420. The tab slot 410 extends into the clip connector 422 from the first surface 445 in a first direction and extends into the clip connector 422 from the second surface 447 in a second, opposite direction. The operator may hold the push tab 420 in order to push the inner connector 226 into the lumen 435 of the clip connector 422 such that the inner connector 226 enters the lumen 435 via the side slot 430 and the push tab 420 enters (e.g., at least partially enters) the clip connector 422 via the tab slot 410. In some examples, the push tab 420 includes a surface feature (e.g., opening, through-hole) that would allow the use of operating room tools (e.g., hemostat) to aid in the positioning of the inner connector 426 (loaded with the tube member) in the final clamped state. As shown in FIG. 4B, an end portion of a tube member 404 is clamped using the push slide clamp connector 402.

Figure 5A:
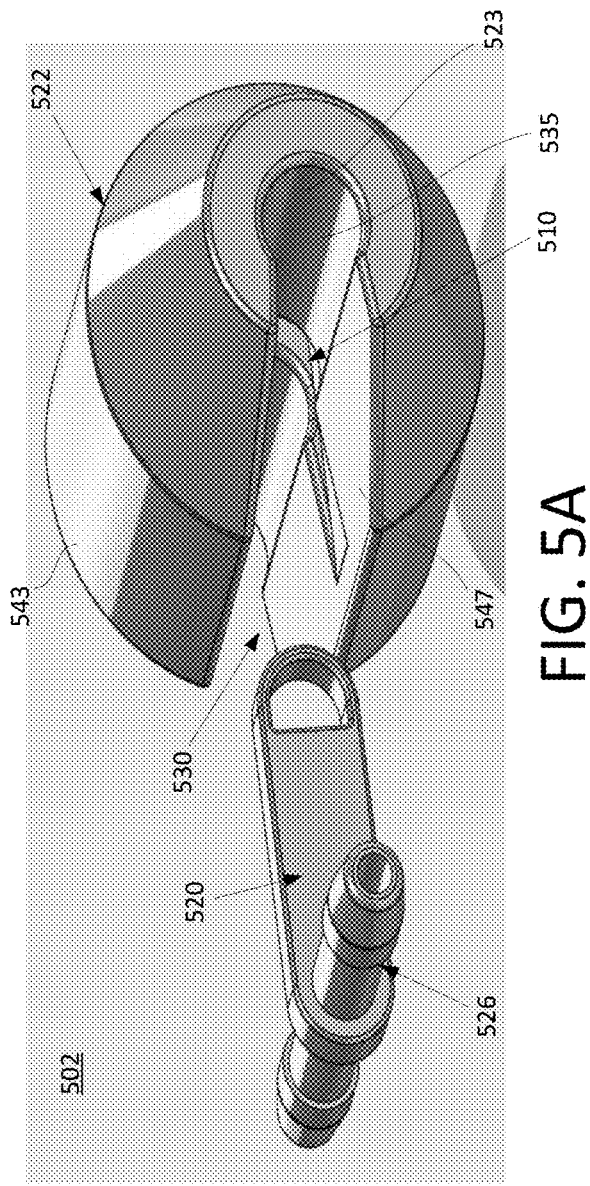
FIG. 5A illustrates a pull slide clamp connector in an unassembled state according to an aspect.
Figure 5B:
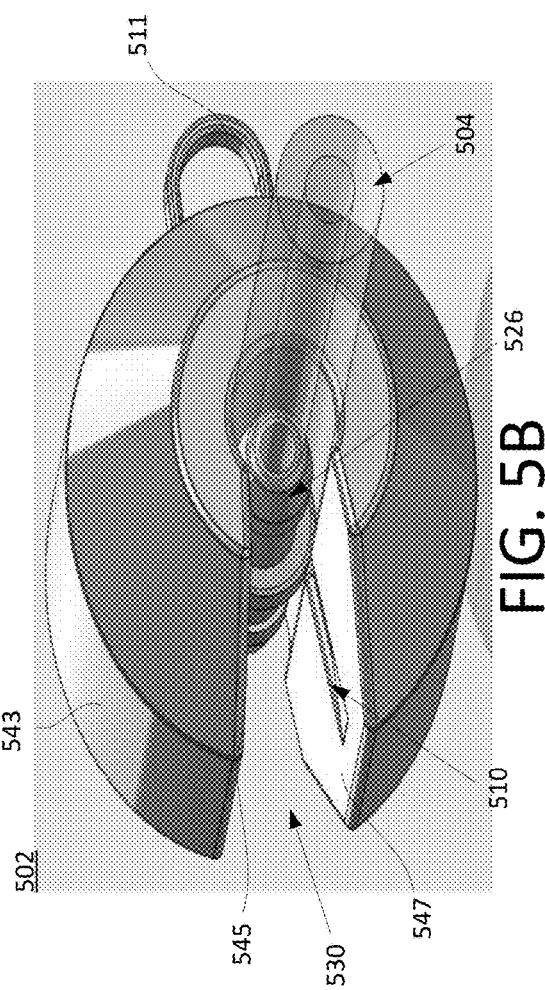
FIG. 5B illustrates the pull slide clamp connector in an assembled state according to an aspect.

FIG. 5A illustrates a perspective of a pull slide clamp connector 502 in an unassembled state according to an aspect. FIG. 5B illustrates a perspective of the pull slide clamp connector 502 in an assembled state according to aspect. The pull slide clamp connector 502 is an example of the connector 102 of FIG. 1. The pull slide clamp connector 502 includes a pull tab 520 integrated with an inner connector 526 (e.g., a ferrule) that is configured to be pulled into an clip connector 522 in order to couple two tube members together.

The inner connector 526 is coupled to the pull tab 520. The inner connector 526 may include any of the features discussed with reference to the inner connector 226 of FIGS. 2A through 2M. In some examples, the inner connector 526 is orthogonal to the pull tab 520. In some examples, the clip connector 522 is a c-shaped connector or collar. The clip connector 522 includes an inner surface 523 and an outer surface 543. The inner surface 523 is curved. The inner surface 523 may define an inner diameter of the clip connector 522. The inner surface 523 defines a lumen 535 along a central axis of the clip connector 522. The outer surface 543 is curved. The outer surface 543 may define an outer diameter of the clip connector 522.

The clip connector 522 defines a side slot 530. The side slot 530 may be a cutout section of the clip connector 522. The side slot 530 extends from the outer surface 543 to the inner surface 523 at a section of the clip connector 522. The side slot 530 defines a first surface 545 and a second surface 547. In some examples, the first surface 545 and the second surface 547 are disposed at an angle with respect to each other such that the side slot 530 is larger towards the outer surface 543. In some examples, the distance between the first surface 545 and the second surface 547 at the inner surface 523 is smaller than a diameter of the inner connector 526 (e.g., smaller than the enlarged ends of the inner connector 526) such that the clip connector 522 expands when the inner connector 526 is inserted into the lumen 535. In some examples, the distance between the first surface 545 and the second surface 547 at the outer surface 543 is larger than the diameter of the inner connector 526 (e.g., larger than the enlarged ends of the inner connector 526).

The clip connector 522 defines a tab slot 510 configured to receive the pull tab 520. In some examples, the pull tab 520 is inserted through the side slot 530 and then through the tab slot 510 until a portion 511 of the pull tab 520 extends from the outer surface 543. In some examples, the portion 511 defines a through-hole (e.g., D-shaped through-hole). Then, an operator may pull the pull tab 520 to place the inner connector 526 into the lumen of the clip connector 522. In some examples, the pull tab 520 includes a surface feature (e.g., opening, through-hole) that would allow the use of operating room tools (e.g., hemostat) to aid in the positioning of the inner connector 526 (loaded with the tube member) in the final clamped state. The tab slot 510 extends from the inner surface 523 to the outer surface 543 at a section of the clip connector 522 that is opposite to the side slot 530. In some examples, the tab slot 510 extends into the clip connector 522 from the first surface 545 in a first direction and extends into the clip connector 522 from the second surface 547 in a second, opposite direction. As shown in FIG. 5B, an end portion of a tube member 504 is clamped using the pull slide clamp connector 502.

Figure 6C:
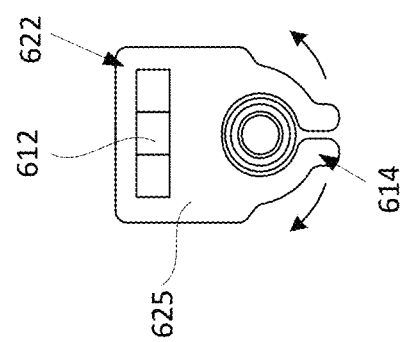
FIG. 6C illustrates a second linear slide member of the linear slide connector according to an aspect.
Figure 6B:
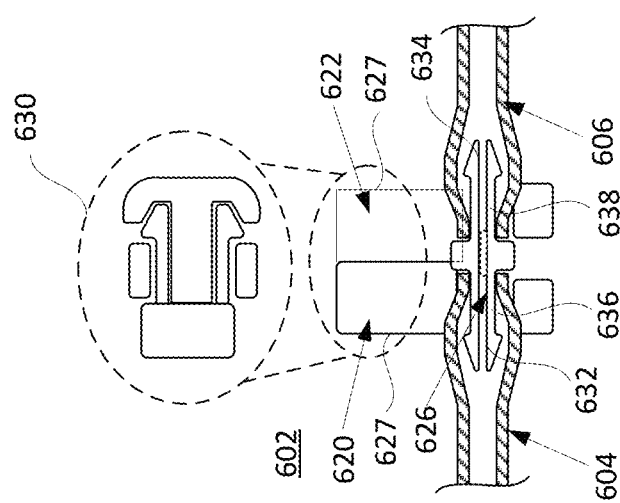
FIG. 6B illustrates the linear slide connector according to an aspect.
Figure 6A:
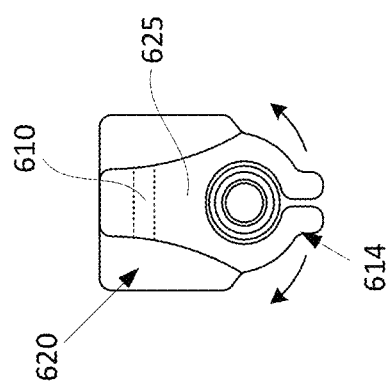
FIG. 6A illustrates a first linear slide member of a linear slide connector according to an aspect.

FIGS. 6A through 6C illustrate a linear slide connector 602 having a first slide member 620 and a second slide member 622 according to an aspect. The linear slide connector 602 is an example of the connector 102 of FIG. 1.

In some examples, the linear slide connector 602 is used with a tool (e.g., a mosquito hemostat) to compress two linear slides (e.g., the first slide member 620 and the second slide member 622) with integrated clip collars 614 (e.g., c-clips). As the first slide member 620 and the second slide member 622 are compressed (e.g., the tool applying pressure to the back surfaces 627 of the members 620, 622), the clip collar 614 of the first slide member 620 expands over a barbed portion 632 of an inner connector 626 (e.g., a ferrule) and the clip collar 614 of the second slide member 622 expands over a barbed portion 634 of the inner connector 626. As the first slide member 620 and the second slide member 622 are further compressed, the clip collar 614 of the first slide member 620 is moved to a shaft portion 636 of the inner connector 626, and the clip collar 614 of the second slide member 622 is moved to a shaft portion 638 of the inner connector 626, which can apply distributed compressed around the shaft portions 636, 638.

The first slide member 620 includes a coupling member 610 configured to lock (e.g., reversibly or irreversible) with a coupling member 612 of the second slide member 622. The coupling member 610 may extend from (or into) an interface surface 625 of the first slide member 620. The coupling member 612 may extend from (or into) an interface surface 625 of the second slide member 622. In some examples, the coupling member 610 and the coupling member 612, collectively, define a linear slide locking mechanism that keeps the members 620, 622 together, and also operates as the final locking mechanism once the members 620, 622 are compressed together. In some examples, the coupling member 610 and the coupling member 612, collectively, a linear slide locking teeth mechanism 630. In some examples, the back surface 627 of the first slide member 620 defines a compressive pad (e.g., recessed feature or flat face), and the back surface 627 of the second slide member 622 defines a compressive pad (e.g., recessed feature or flat face) that provides a hemostat the ability to easily squeeze the members 620, 622 together under a compressive load without slipping off.

Figure 7:
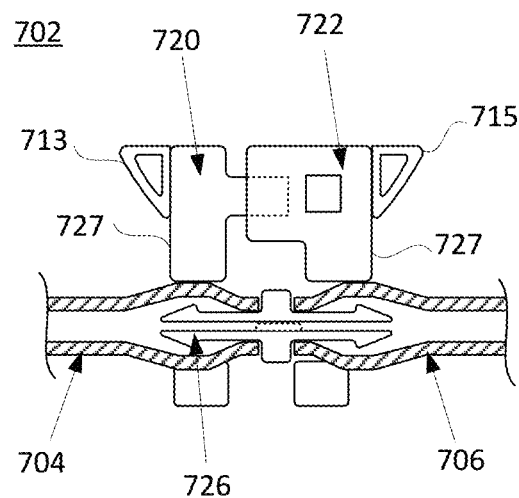
FIG. 7 illustrates a linear slide connector according to another aspect.

FIG. 7 illustrates a linear slide connector 702 having a first slide member 720 and a second slide member 722 in an assembled state over an inner connector 726 in order to couple a first tube member 704 with a second tube member 706. The linear slide connector 702 may include any of the features discussed with reference to the linear slide connector 602 of FIGS. 6A through 6C. However, as shown in FIG. 7, the first slide member 720 may include a loop 713 extending from a back surface 727 of the first slide member 720, and a loop 715 extending from a back surface 727 of the second slide member 722. In some examples, a hemostat may connect to the loop 713 and the loop 715 in order to compress the members 720, 722 together. In other examples, the loop 713 and the loop 715 may be used as a feature to anchor the linear slide connector 702 to surrounding tissue.

Figure 8B:
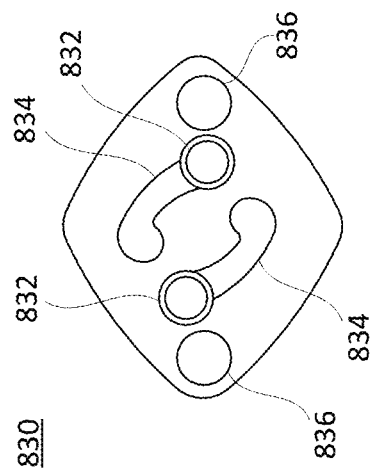
FIG. 8B illustrates the rotating disc according to an aspect.
Figure 8A:
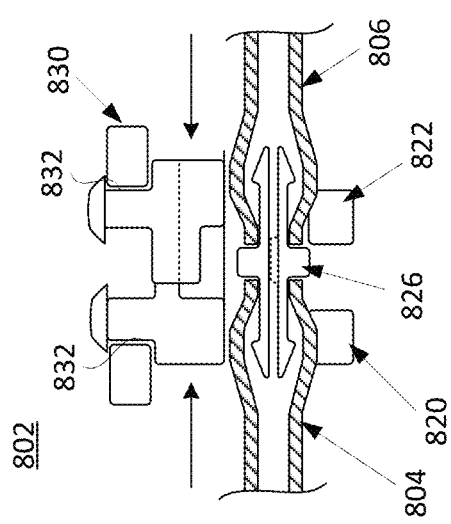
FIG. 8A illustrates a linear slide connector with a rotating disc according to an aspect.

FIGS. 8A through 8B illustrate a linear slide connector 802 having a quarter-turn disc 830 according to an aspect. The linear slide connector 802 includes a first slide member 820 and a second slide member 822. The first slide member 820 and the second slide member 822 are configured to be disposed over an inner connector 826 and compressed together (and locked) in order to couple a first tube member 804 with a second tube member 806.

The linear slide connector 802 may include any of the features discussed with reference to the linear slide connector 602 of FIGS. 6A through 6C and/or the linear slide connector 702 of FIG. 7. However, as shown in FIG. 8, the linear slide connector 802 uses the quarter-turn disc 830 (e.g., rotating or twisting the quarter-turn disc 830) to pull the first slide member 820 and the second slide member 822 together. The quarter-turn disc 830 may define cam slots 832, cam followers 834, and holes 836. The holes 836 may be used for the hemostat to grip, or may be used for suturing. The linear slide connector 802 allows the operator to rotate the quarter-turn disc 830 with their fingertips (or using a hemostat inserted into the holes 836) to turn the quarter-turn disc 830 to lock the first slide member 820 and the second slide member 822 together.

Figure 9:
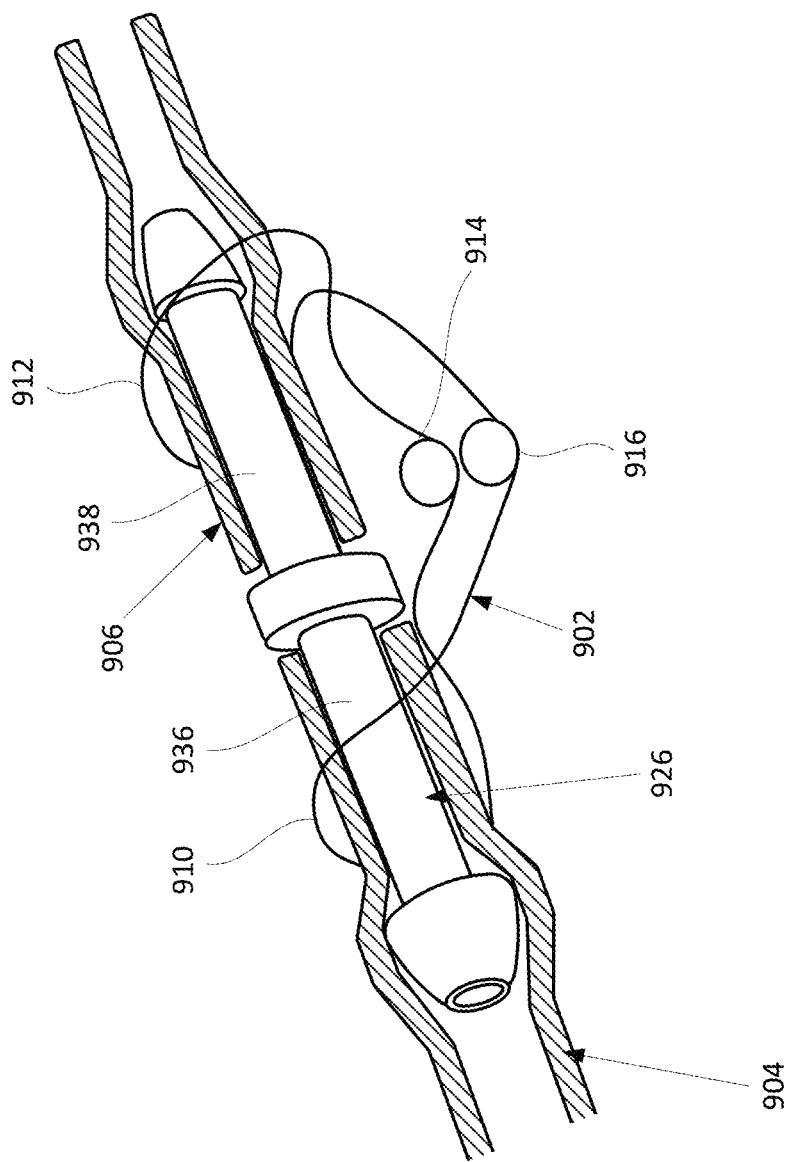
FIG. 9 illustrates a spring clamp connector according to an aspect.

FIG. 9 illustrates a spring clamp connector 902 according to an aspect. The spring clamp connector 902 is an example of the connector 102 of FIG. 1. As shown in FIG. 9, a first tube member 904 is disposed over a shaft portion 936 of an inner connector 926, and a second tube member 906 is disposed over a shaft portion 938 of the inner connector 926. The spring clamp connector 902 is configured to hold the first tube member 904 and the second tube member 906 together by compressing the first tube member 904 and the second tube member 906 against the shaft portion 936 and the shaft portion 938, respectively.

The spring clamp connector 902 is a wire-form. The wire-form may include stainless steel, Nitinol, and/or Titanium in either diametric wire or ribbon form. The spring clamp connector 902 defines a first compression loop 910 (disposed around the first tube member 904, and a second compression loop 912 (disposed around the second tube member 906). Also, the spring clamp connector 902 defines a first connector loop 914 and a second connector loop 916. In some examples, the spring clamp connector 902 is assembled and packaged in a tensioned state. The spring clamp connector 902 may be compressed with a hemostat (e.g., using the first connector loop 914 and the second connector loop 916), and then the members 904, 906 are placed over the inner connector 926. When released from the compressed state, the first compression loop 910 becomes smaller (or tightens) to compress the first tube member 904 against the shaft portion 936, and the second compression loop 912 becomes smaller (or tightens) to compress the second tube member 906 against the shaft portion 938.

Figure 10:
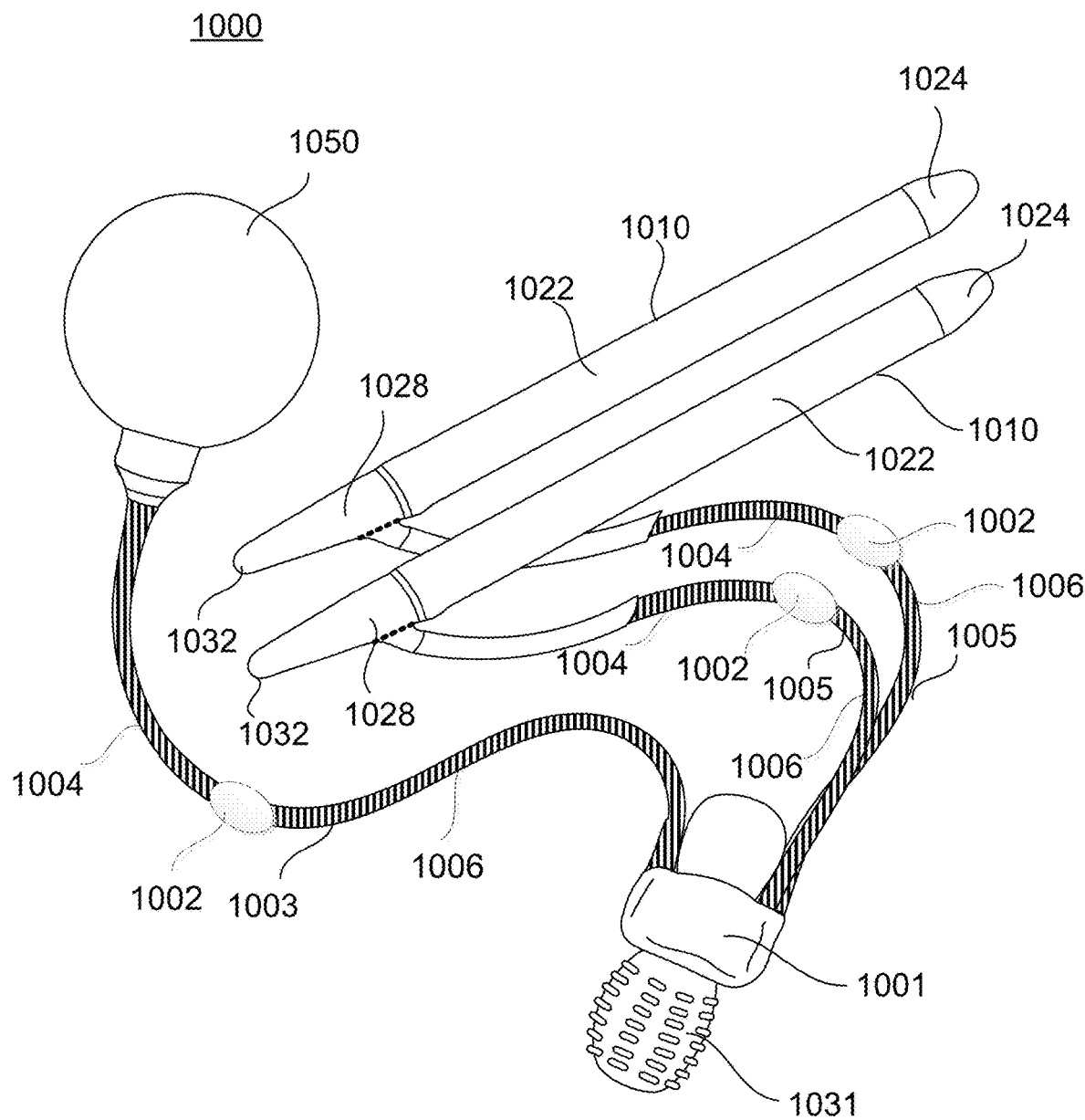
FIG. 10 schematically illustrates an inflatable penile prosthesis having one or more connectors according to an aspect.

FIG. 10 schematically illustrates an inflatable penile prosthesis 1000 having one or more connectors 1002 according to an aspect. The connectors 1002 may be any of the connectors (e.g., 102, 202, 302, 402, 502, 602, 702, 802, 902) described with reference to the previous figures. The penile prosthesis 1000 may include a pair of cylinders 1010, and the pair of cylinders or inflatable members 1010 are configured to be implanted in a penis. For example, one of the cylinders 1010 may be disposed on one side of the penis, and the other cylinder 1010 of the pair of cylinders may be disposed on the other side of the penis. The cylinder 1010 may include a first end portion 1024, a cavity or inflation chamber 1022, and a second end portion 1028 having a rear tip 1032.

The penile prosthesis 1000 may include a pump assembly 1001, which may be implanted into the patient's scrotum. A pair of conduit connectors 1005 may attach the pump assembly 1001 to the pair of inflatable members or cylinders 1010 such that the pump assembly 1001 is in fluid communication with the pair of inflatable members or cylinders 1010. In some examples, the conduit connector 1005 includes a first tube member 1004, and a second tube member 1006 that is separated from the first tube member 1004 but connected together using the connector 1002.

Also, the pump assembly 1001 may be in fluid communication with a reservoir 1050 via a conduit connector 1003. In some examples, the conduit connector 1003 includes a first tube member 1004 and a second tube member 1006 that is separate from the first tube member 1004 but connected together using the connector 1002. The reservoir 1050 may be implanted into the user's abdomen. The inflation chamber or portion 1022 of the cylinder 1010 may be disposed within the penis. The first end portion 1024 of the cylinder 1010 may be at least partially disposed within the crown portion of the penis. The second end portion 1028 may be implanted into the patient's pubic region PR with the rear tip 1032 proximate the pubic bone PB.

In order to implant the inflatable members or cylinders 1010, the surgeon first prepares the patient. The surgeon often makes an incision in the penoscrotal region, e.g., where the base of the penis meets with the top of the scrotum. From the penoscrotal incision, the surgeon may dilate the patient's corpus cavernosae to prepare the patient to receive the pair of inflatable members or cylinders 1010. The corpus cavernosum is one of two parallel columns of erectile tissue forming the dorsal part of the body of the penis, e.g., two slender columns that extend substantially the length of the penis. The surgeon will also dilate two regions of the pubic area to prepare the patient to receive the second end portion 1028. The surgeon may measure the length of the corpora cavernosae from the incision and the dilated region of the pubic area to determine an appropriate size of the inflatable members or cylinders 1010 to implant.

After the patient is prepared, the penile prosthesis 1000 is implanted into the patient. The tip of the first end portion 1024 of each cylinder 1010 may be attached to a suture. The other end of the suture may be attached to a needle member (e.g., Keith needle). The needle member is inserted into the incision and into the dilated corpus cavernosum. The needle member is then forced through the crown of the penis. The surgeon tugs on the suture to pull the cylinder 1010 into the corpus cavernosum. This is done for each cylinder of the pair of cylinders 1010. Once the inflation chamber 1022 is in place, the surgeon may remove the suture from the tip. The surgeon then inserts the second end portion 1028. The surgeon inserts the rear end of the cylinder 1010 into the incision and forces the second end portion 1028 toward the pubic bone PB until each cylinder 1010 is in place.

A pump bulb 1031 of the pump assembly 1001 may be squeezed or depressed by the user in order to facilitate the transfer of fluid from the reservoir 1050 to the cylinders 1010. For example, in the inflation mode, while the user is operating the pump bulb 1031, the pump bulb 1031 may receive the fluid from the reservoir 1050, and then output the fluid to the cylinders 1010. When the user switches to the deflation mode, at least some of the fluid can automatically be transferred back to the reservoir 1050 (due to the difference in pressure from the cylinders 1010 to the reservoir 1050). Then, the user may squeeze the cylinders 1010 to facilitate the further transfer of fluid through the pump bulb 1031 to the reservoir 1050.

Figure 11:
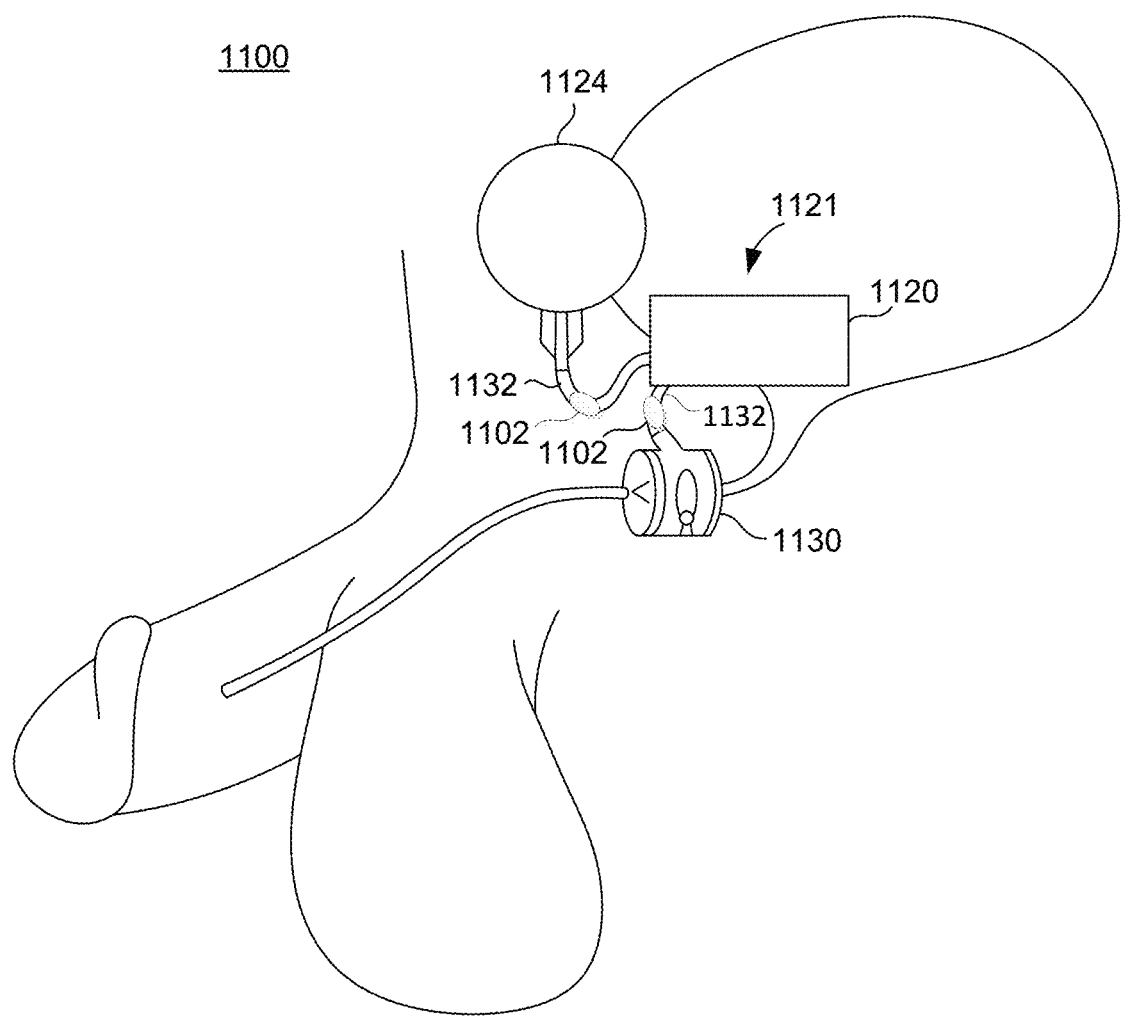
FIG. 11 illustrates a urinary control system having one or more connectors according to an aspect.

FIG. 11 illustrates a urinary control system 1100 having one or more connectors 1102 according to an aspect. The connectors 1102 may be any of the connectors (e.g., 102, 202, 302, 402, 502, 602, 702, 802, 902) described with reference to the previous figures.

The artificial urinary sphincter ("AUS") system 1100 includes a pump 1120 attached to a pressure-regulating inflation balloon or element 1124. The inflation element 1124 is likewise in operative fluid communication with the cuff 1130 via one or more tube members 1132, chambers, valves or similar structures. In some examples, the tube members 1132 are coupled together using the connector 1102. The inflation element 1124 is constructed of polymer material that is capable of elastic deformation to reduce fluid volume within the inflation element 1124 and push fluid out of the inflation element 1124 and into the cuff 1130. However, the material of the inflation element 1124 can be biased or include a shape memory construct adapted to generally maintain the inflation element 1124 in its expanded state with a relatively constant fluid volume and pressure. In some examples, this constant level of pressure exerted from the inflation element 1124 to the cuff 1130 will keep the cuff 1130 at a desired inflated state when open fluid communication is provided between the inflation element 1124 and the cuff 1130. This is largely due to the fact that only a small level of fluid displacement is required to inflate or deflate the cuff 1130. In some examples, the inflation element 1124 is implanted into the abdominal space.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A bodily implant comprising:
   a connector configured to connect a first tube member and a second tube member such that fluid can be transferred through the first tube member and the second tube member, the connector including:
   a first clip member having an inner surface;
   a second clip member having an inner surface;
   a hinge member coupled to the first clip member and the second clip member;
   a retaining member coupled to the inner surface of the second clip member; and
   an inner connector coupled to the retaining member,
   wherein the retaining member defines an opening, a portion of the inner connector being disposed within the opening.

2. The bodily implant of claim 1, wherein the inner connector is movably coupled to the retaining member, when the connecter is in an open state.

3. The bodily implant of claim 1, wherein the retaining member includes a retaining clip that is coupled to the second clip member.

4. The bodily implant of claim 1, wherein the connector is configured to move from an open position to a closed position, in the closed position, the first clip member being disposed on top of the second clip member such that the inner surface of the first clip member and the inner surface of the second clip member define a lumen.

5. The bodily implant of claim 4, wherein the first clip member includes a coupling member, and the second clip member includes a coupling member, in the closed position, the coupling member of the first clip member engages the coupling member of the second clip member to assist with keeping the connector in the closed position.

6. The bodily implant of claim 5, wherein the coupling member of the first clip member and the coupling member of the second clip member, collectively, define a snap-fit joint connection.

7. The bodily implant of claim 1, wherein the hinge member includes a flexible portion.

8. The bodily implant of claim 1, wherein the first clip member includes an outer surface, the outer surface including a curved portion and a planar portion.

9. The bodily implant of claim 1, wherein the inner connector defines a lumen.

10. The bodily implant of claim 1, wherein the inner surface of the first clip member includes a plurality of protrusions.

11. A bodily implant comprising:
    a connector configured to connect a first tube member and a second tube member such that fluid can be transferred through the first tube member and the second tube member, the connector including:
    a first clip member having an inner surface;
    a second clip member having an inner surface;
    a hinge member coupled to the first clip member and the second clip member, the hinge member including a flexible member;
    a retaining member coupled to the inner surface of the second clip member; and
    an inner connector coupled to the retaining member,
    wherein the retaining member includes an opening and a retaining portion that is coupled to the second clip member, a portion of the inner connector being disposed within the opening.

12. The bodily implant of claim 11, wherein the connector is configured to move from an open position to a closed position, in the closed position, the first clip member being disposed on top of the second clip member such that the inner surface of the first clip member and the inner surface of the second clip member define a lumen.

13. The bodily implant of claim 12, wherein the first clip member includes a coupling member, and the second clip member includes a coupling member, in the closed position, the coupling member of the first clip member engages the coupling member of the second clip member to assist with keeping the connector in the closed position.

14. The bodily implant of claim 11, wherein the first clip member includes an outer surface, the outer surface including a curved portion and a planar portion.

15. A bodily implant comprising:
    a connector configured to connect a first tube member and a second tube member such that fluid can be transferred through the first tube member and the second tube member, the connector including:
    a first clip member having an inner surface and an outer surface, the outer surface of the first clip member having a convex portion and a planar portion, the planar portion of the outer surface of the first clip member being configured to receive a portion of a tool;
    a second clip member having an inner surface and an outer surface, the outer surface of the second clip member having a convex portion and a planar portion, the planar portion of outer surface of the second clip member being configured to receive a portion of the tool;
    a hinge member coupled to the first clip member and the second clip member;
    a retaining member coupled to the inner surface of the second clip member; and
    an inner connector coupled to the retaining member.

16. The bodily implant of claim 15, wherein the retaining member includes an opening and a retaining portion that is coupled to the second clip member, a portion of the inner connector being disposed within the opening.

17. The bodily implant of claim 15, wherein the connector is configured to move from an open position to a closed position, in the closed position, the first clip member being disposed on top of the second clip member such that the inner surface of the first clip member and the inner surface of the second clip member define a lumen.

18. The bodily implant of claim 17, wherein the first clip member includes a coupling member, and the second clip member includes a coupling member, in the closed position, the coupling member of the first clip member engages the coupling member of the second clip member to assist with keeping the connector in the closed position.

19. The bodily implant of claim 15, wherein the hinge member includes a flexible portion.

* * * * *